(12) United States Patent
Houben et al.

(10) Patent No.: US 9,380,953 B2
(45) Date of Patent: Jul. 5, 2016

(54) HYBRID BIPOLAR/UNIPOLAR DETECTION OF ACTIVATION WAVEFRONT

(71) Applicant: BIOSENSE WEBSTER (ISRAEL) LTD., Yokneam (IL)

(72) Inventors: Richard P. M. Houben, Lanaken (BE); Meir Bar-Tal, Haifa (IL); Lior Botzer, Timrat (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 14/166,982

(22) Filed: Jan. 29, 2014

(65) Prior Publication Data
US 2015/0208938 A1   Jul. 30, 2015

(51) Int. Cl.
*A61B 5/04* (2006.01)
*A61B 5/042* (2006.01)
*A61B 5/00* (2006.01)
*A61B 5/0452* (2006.01)

(52) U.S. Cl.
CPC ............ *A61B 5/04012* (2013.01); *A61B 5/042* (2013.01); *A61B 5/04017* (2013.01); *A61B 5/0422* (2013.01); *A61B 5/0452* (2013.01); *A61B 5/72* (2013.01); *A61B 5/7203* (2013.01); *A61B 5/7239* (2013.01); *A61B 5/7246* (2013.01)

(58) Field of Classification Search
USPC .................................................. 600/508–509
See application file for complete search history.

(56) References Cited

U.S. PATENT DOCUMENTS

| | | | |
|---|---|---|---|
| 5,546,951 | A | 8/1996 | Ben-Haim |
| 5,601,088 | A | 2/1997 | Swanson et al. |
| 5,738,096 | A | 4/1998 | Ben-Haim |
| 6,226,542 | B1 | 5/2001 | Reisfeld |
| 6,236,883 | B1 | 5/2001 | Ciaccio |
| 6,301,496 | B1 | 10/2001 | Reisfeld |
| 6,669,692 | B1 | 12/2003 | Nelson |
| 6,690,963 | B2 | 2/2004 | Ben-Haim et al. |
| 6,892,091 | B1 | 5/2005 | Ben-Haim et al. |
| 7,245,962 | B2 | 7/2007 | Ciaccio |

(Continued)

FOREIGN PATENT DOCUMENTS

| | | |
|---|---|---|
| EP | 0202748 B1 | 7/1990 |
| WO | WO 96/05768 A1 | 2/1996 |

(Continued)

OTHER PUBLICATIONS

Anderson, K. P., et al., "Determination of Local Myocardial Electrical Activation for Activation Sequence Mapping", Circulation Research (1991), vol. 69, pp. 898-917.

(Continued)

*Primary Examiner* — Nicole F Lavert
(74) *Attorney, Agent, or Firm* — Notaro, Michalos & Zaccaria P.C.

(57) ABSTRACT

A bipolar electrogram and a unipolar electrogram are recorded from electrodes of a probe, and differentiated with respect to time. Peaks are identified in the differentiated bipolar electrogram. An activity window is defined that includes bipolar activity about the peaks. An extreme negative value in the differentiated unipolar electrogram within the activity window is reported as a unipolar activation onset. In one aspect, an annotation is selected from candidate minima in the differentiated unipolar electrogram within the activity window by excluding candidates that fail to correlate with activity in the bipolar electrogram.

26 Claims, 20 Drawing Sheets

(56) References Cited

U.S. PATENT DOCUMENTS

| | | |
|---|---|---|
| 2009/0099468 A1 | 4/2009 | Thiagalingam et al. |
| 2010/0074482 A1 | 3/2010 | Toth et al. |
| 2010/0191132 A1 | 7/2010 | Jackson |
| 2012/0184865 A1* | 7/2012 | Harlev ............... A61B 5/7475 600/509 |
| 2013/0019945 A1 | 1/2013 | Hekmatshoar-Tabari |
| 2013/0109945 A1 | 5/2013 | Harlev et al. |

FOREIGN PATENT DOCUMENTS

| | | |
|---|---|---|
| WO | WO 2008/038220 A1 | 4/2008 |
| WO | WO 2009/020167 A1 | 2/2009 |
| WO | WO 2012/092016 A1 | 7/2012 |
| WO | WO 2012/151301 A1 | 11/2012 |
| WO | WO 2013/123549 A1 | 8/2013 |

OTHER PUBLICATIONS

Ndrepepa, G., et al., "Activation Time Determination by High-Resolution Unipolar and Bipolar Extracellular Electrograms in the Canine Heart", Journal of Cardiovascular Electrophysiology, vol. 6, No. 3 (Mar. 1995) p. 174-188.

Ye, H. He, et al., "An Interactive Graphical System for Automated Mapping and Display of Cardiac Rhythms", Journal for Electrocardiology, vol. 32, No. 3 (1999) pp. 225-241.

European Search Report received Jun. 30, 2015 for Application No. EP15152788.

* cited by examiner

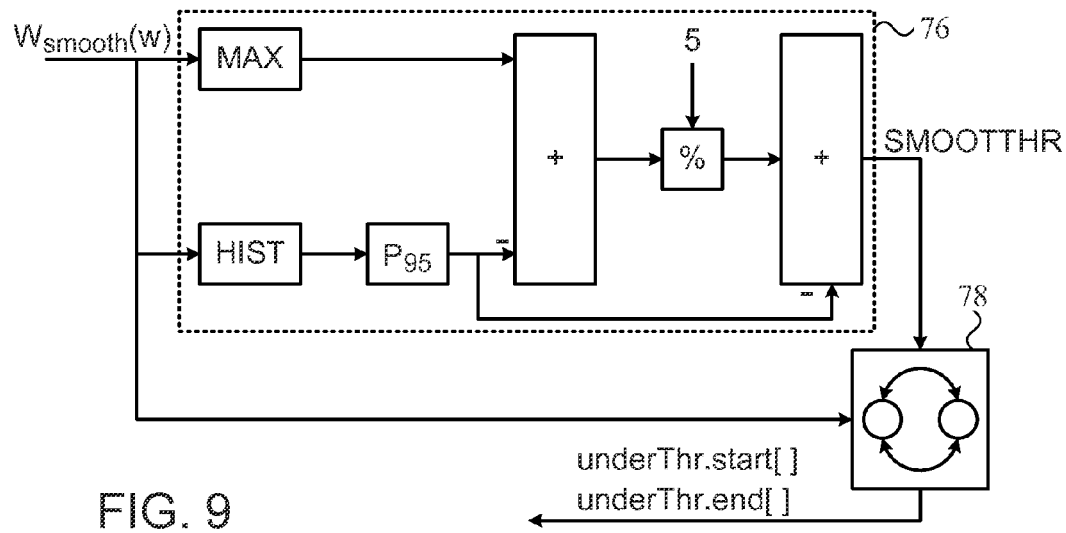
FIG. 9
FIG. 10
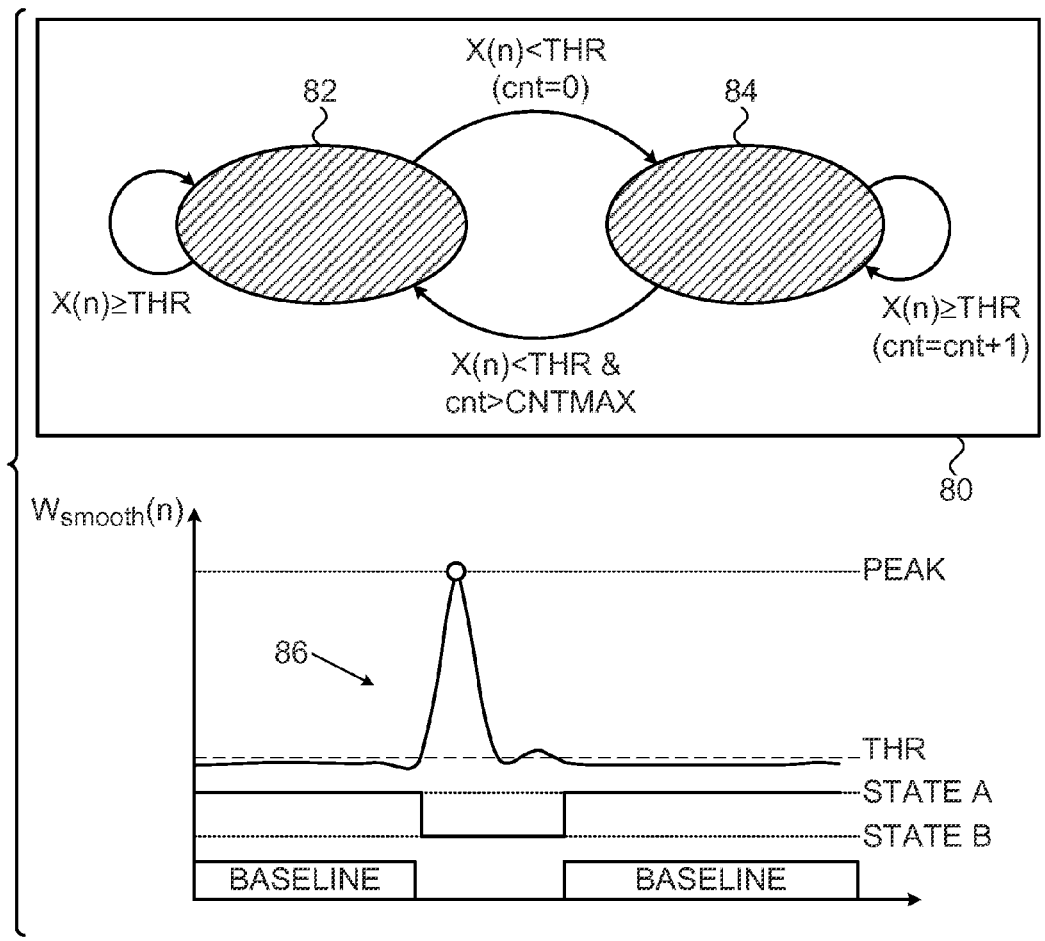

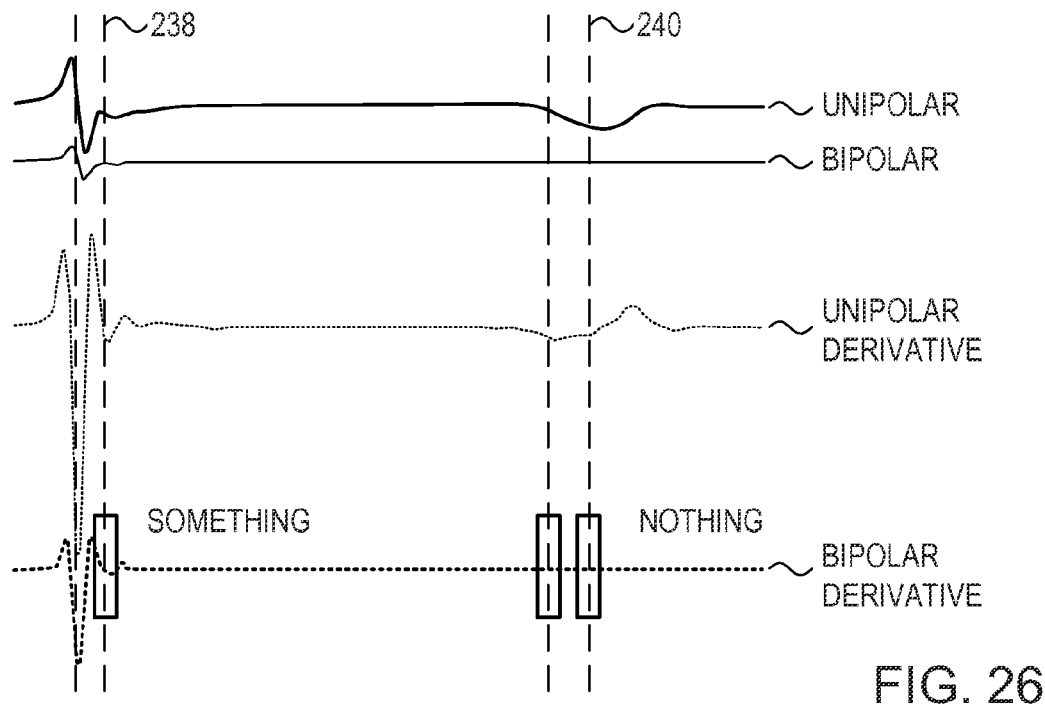
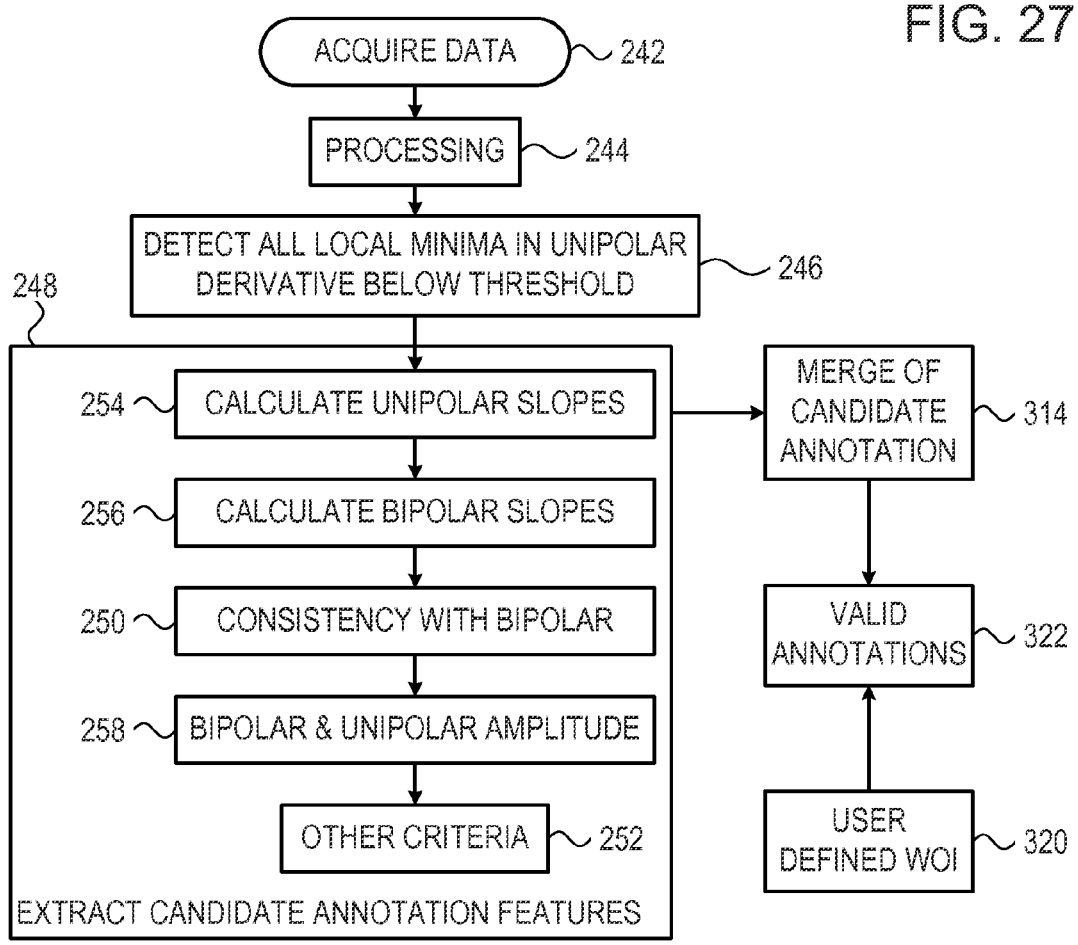
FIG. 26
FIG. 27

HYBRID BIPOLAR/UNIPOLAR DETECTION OF ACTIVATION WAVEFRONT

BACKGROUND OF THE INVENTION

1. Field of the Invention

This invention relates to cardiac physiology. More particularly, this invention relates to the evaluation of electrical propagation in the heart.

2. Description of the Related Art

The meanings of certain acronyms and abbreviations used herein are given in Table 1.

TABLE 1

Acronyms and Abbreviations

| | |
|---|---|
| CFAE | Complex Fractionated Atrial Electrogram |
| ECG | Electrocardiogram |
| EGM | Electrogram |
| FIR | finite impulse response |
| IIR | infinite impulse response |
| LAT | Local Activation Time |
| LPF | low pass filter |
| RMS | root-mean-square |
| SNR | signal-to-noise ratio |
| UEGM | Unipolar Electrogram |

Cardiac arrhythmias such as atrial fibrillation are an important cause of morbidity and death. Commonly assigned U.S. Pat. No. 5,546,951, and U.S. Pat. No. 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. No. 6,226,542, and U.S. Pat. No. 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

However, determination of local activation time as an indicator of electrical propagation becomes problematic in the presence of conduction abnormalities. For example, atrial electrograms during sustained atrial fibrillation have three distinct patterns: single potential, double potential and a complex fractionated atrial electrograms (CFAE's).

SUMMARY OF THE INVENTION

Current available algorithms for onset detection measure the local activation time (LAT) based on local maximum or minimum amplitude detection (peak detection) or slope (slope detection) of bipolar recordings. Especially in more complex activation of either the atria or ventricles of the heart, these methods are of limited value in supporting correct mapping and diagnosis of tachycardias. Detection ambiguities arise from at least the following two factors: (1) complex recordings, showing potentials with multiple peaks; and (2) a mixture of two electrograms recorded at two different sites. As a result, the morphology of a bipolar electrogram is largely determined by the phase difference between the activation at the two poles. During more complex activation, the direction of propagation changes continuously, thereby introducing a higher spatiotemporal variation in morphology in bipolar electrograms compared to unipolar electrograms. Tissue anisotropy influences the shape of electrograms, but the overall morphology of unipolar electrograms is far less affected by changes in direction than are bipolar electrograms.

There is provided according to embodiments of the invention a method, which is carried out by inserting a probe into a heart of a living subject, recording a bipolar electrogram and a unipolar electrogram from a location in the heart with electrodes of the probe, defining a time interval comprising a window-of-interest, and differentiating the bipolar electrogram and the unipolar electrogram with respect to time. The method is further carried out by identifying peaks within the window-of-interest in the differentiated bipolar electrogram, and establishing a bipolar activity window having activity bounds that include bipolar activity about respective peaks. The method is further carried out by identifying an extreme negative value ($-dV/dt$) in the differentiated unipolar electrogram within the activity bounds, and reporting a time corresponding to the value as a unipolar activation onset.

An aspect of the method includes filtering the unipolar electrogram to remove baseline wander therefrom.

According to another aspect of the method, identifying an extreme negative value includes defining a slope window in the unipolar electrogram that contains downward sloping intervals, fitting respective regression lines to the downward sloping intervals, determining a trend in the slope window, identifying a longest monotonic downward sloping interval contained in each slope window, making a determination that the longest monotonic downward sloping interval occupies less than 50% of its containing slope window, and responsive to the determination subtracting the slope of the trend from a slope of the regression line of the longest monotonic downward sloping interval.

Another aspect of the method includes iterating the steps of identifying peaks, establishing a bipolar activity window and identifying an extreme negative value using time-reversed versions of the bipolar electrogram and the differentiated unipolar electrogram as the differentiated bipolar electrogram to yield a new extreme negative value, and reporting a time corresponding to the new extreme negative value as a unipolar activation termination.

According to still another aspect of the method, establishing a bipolar activity window includes defining baseline segments between complexes of the bipolar electrogram, identifying the complexes by executing a state machine, and assigning a transition between the baseline segments and the complexes as a boundary of the bipolar activity window.

According to an additional aspect of the method, establishing a bipolar activity window includes classifying segments in the bipolar electrogram as being above or below a predefined value, and identifying a transition from one of the segments to another of the segments as a boundary of the bipolar activity window.

There is further provided according to embodiments of the invention a method, which is carried out by inserting a probe into a heart of a living subject, recording a bipolar electrogram and a unipolar electrogram from a location in the heart with the electrodes, and differentiating the bipolar electrogram and the unipolar electrogram with respect to time. The method is further carried out by assigning respective times corresponding to minima in the differentiated unipolar electrogram as candidate annotation points, wherein the minima are less than a predefined negative threshold value, defining respective time intervals about the minima, determining that during at least one of the time intervals the bipolar electrogram or the differentiated bipolar electrogram fails to meet a criterion of correlated activity with the differentiated unipolar electrogram, and defining qualified candidate annotation points by excluding candidate annotation points that lie within the at least one time interval. The method is further carried out by establishing an annotation as an activation onset time in the unipolar electrogram from among the qualified candidate annotation points, and reporting the annotation.

Another aspect of the method includes adjusting the bipolar electrogram and the unipolar electrogram to null baseline portions thereof.

According to one aspect of the method, adjusting includes filtering the unipolar electrogram with a median filter.

According to an additional aspect of the method, adjusting includes filtering the bipolar electrogram with a median filter.

According to one aspect of the method, the criterion of correlated activity includes a variation of amplitude in the bipolar electrogram.

According to a further aspect of the method, the variation of amplitude is at least 0.008 mV.

According to another aspect of the method, the criterion of correlated activity includes a failure of a slope of the bipolar electrogram to exceed −0.008 mV/ms.

According to one aspect of the method, the criterion of correlated activity comprises a ratio between a slope of the bipolar electrogram and a slope of the unipolar electrogram that exceeds 0.2.

According to a further aspect of the method, the criterion of correlated activity comprises a ratio between an amplitude of the bipolar electrogram and an amplitude of the unipolar electrogram that exceeds a predetermined value.

According to yet another aspect of the method, the time intervals have boundaries located ±2 ms from the candidate annotation points.

According to still another aspect of the method, a slope of the unipolar electrogram at the candidate annotation points does not exceed −0.01 mV/ms.

In an additional aspect of the method establishing an annotation includes determining that a plurality of the qualified candidate annotation points constitute a single activity according to a predetermined single activity criterion, merging the plurality of the qualified candidate annotation points into a merged candidate annotation, and selecting one annotation from the merged candidate annotation and others of the qualified candidate annotation points.

According to yet another aspect of the method, the single activity criterion includes a determination that a peak in the differentiated unipolar electrogram lies between two qualified candidate annotation points and a ratio between (1) a difference between the peak and one of the two qualified candidate annotation points and (2) another of the two qualified candidate annotation points exceeds a predefined ratio.

There is further provided according to embodiments of the invention apparatus for carrying out the above-described methods.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 9 is a data flow diagram illustrating an embodiment of a portion of the method shown in FIG. 3 in accordance with an embodiment of the invention;

FIG. 10 is a schematic diagram illustrating the operation of a state machine shown FIG. 9, in accordance with an embodiment of the invention;

FIG. 26 is a graph illustrating separation between local activation and far field activity based on correlated and uncorrelated electrical activities in bipolar and unipolar electrograms, in accordance with an embodiment of the invention;

FIG. 27 is a flow chart of a method of activation detection in unipolar and bipolar electrograms, in accordance with an alternate embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Definitions

"Annotations" or "annotation points" refer to points or candidates on an electrogram that are considered to denote events of interest. In this disclosure the events are typically onset (local activation time) of the propagation of an electrical wave as sensed by the electrode.

"Trend" refers to the slope of a regression line fitted to an interval of an electrogram. It often serves as a reference when evaluating a change in the values of a subinterval of the tracing.

"Activity" in an electrogram is used herein to denote a distinct region of bursty or undulating changes in an electrogram signal. Such a region may be recognized as being outstanding between regions of baseline signals. In this disclosure "activity" more often refers to a manifestation on an electrogram of one or more electrical propagation waves through the heart.

System Architecture

Figure 1:
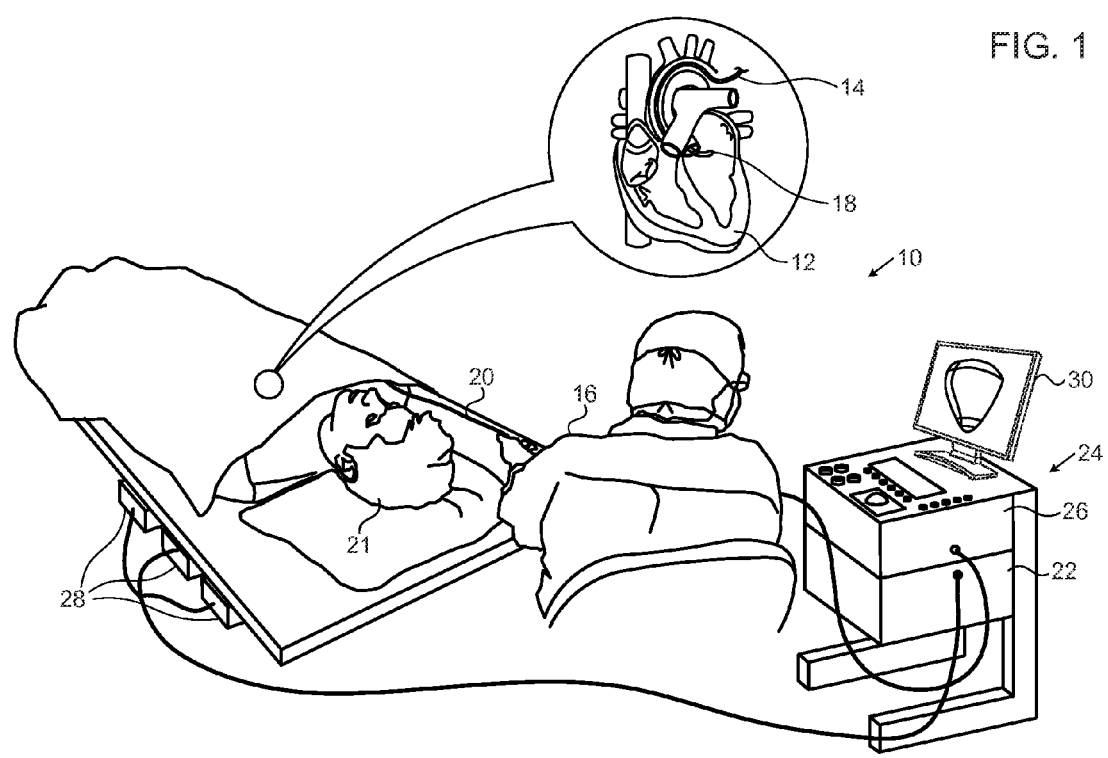
FIG. 1 is a pictorial illustration of a system for detecting areas of abnormal electrical activity in a heart of a living subject in accordance with an embodiment of the invention.

Turning now to the drawings, reference is initially made to FIG. 1, which is a pictorial illustration of a system 10 for detecting areas of electrical activity in a heart 12 of a living subject 21 in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Unipolar and bipolar electrograms are recorded using mapping electrodes on the distal segment of the catheter. Electrical activation maps based on the electrograms are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14 may be adapted, mutatis mutandis, from the ablation catheter described in commonly assigned U.S. Pat. No. 6,669,692, whose disclosure is herein incorporated by reference. The console 24 typically contains an ECG processor 26 and a display 30.

The positioning processor 22 measures location and orientation coordinates of the catheter 14. In one embodiment, the system 10 comprises a magnetic position tracking system that determines the position and orientation of the catheter 14. The system 10 typically comprises a set of external radiators, such as field generating coils 28, which are located in fixed, known positions external to the patient. The coils 28 generate electromagnetic fields in the vicinity of the heart 12. These fields are sensed by magnetic field sensors located in the catheter 14.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. The system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling an ablation site may be provided.

One system that embodies the above-described features of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein. Multi-electrode basket and spline catheters are known that are suitable for obtaining unipolar and bipolar electrograms. An example of such a spline catheter is the Pentaray® NAV catheter, available from Biosense Webster.

In this disclosure references are made to negative values and downsloping segments of electrograms and their derivatives which are conventional in the art. It will of course be understood that these references also contemplate cases in which polarities have been reversed to manifest positive values and upsloping segments.

Unipolar Annotation Embodiment

Figure 2:
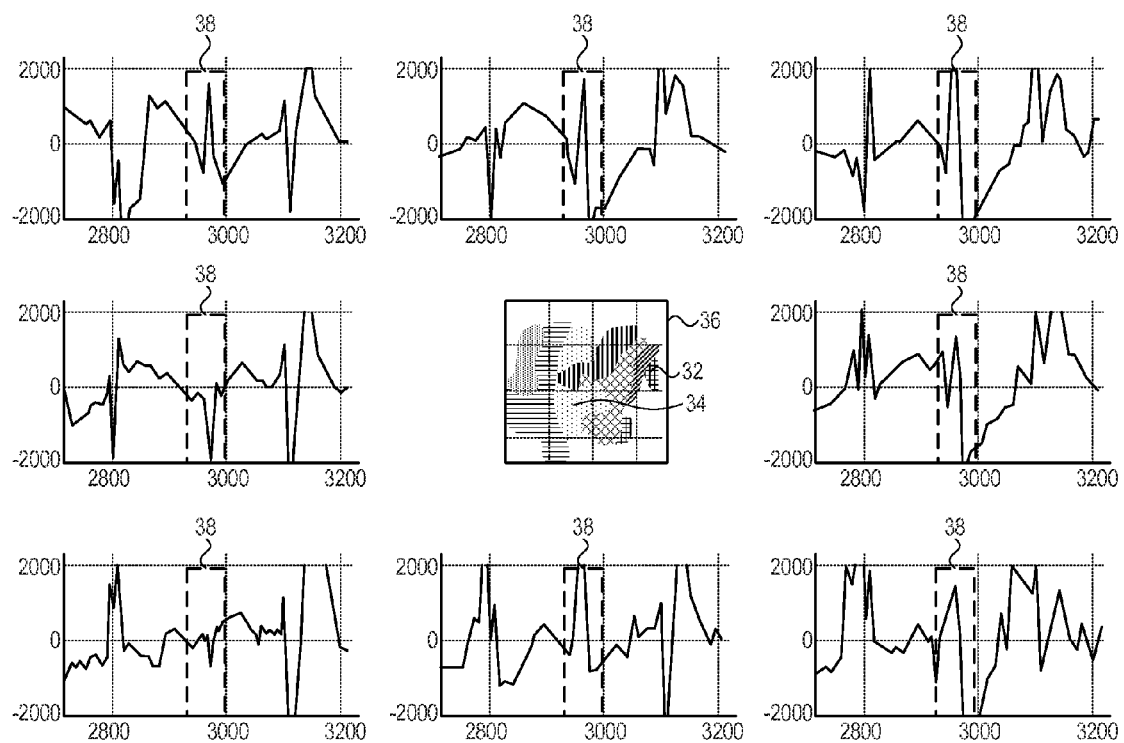
FIG. 2 is a group of bipolar electrograms for evaluation in accordance with an embodiment of the invention.

In order to better illustrate the difficulties that can be solved by application of the principles of the invention, reference is now made to FIG. 2, which is a group of bipolar electrograms, in accordance with an embodiment of the invention in which a simulated bipolar electrode has been positioned in eight directions. The bipolar electrograms have been calculated from the difference of unipolar electrograms e.g., squares 32, 34, shown in distinctive hatching patterns in an electroanatomic map 36, in which one pole is fixedly positioned at the square 32 and the other pole is rotated in 8 steps (4 perpendicular and four oblique positions) around the position of the fixed pole. On the map 36, an activation wave propagates slightly obliquely from right to left. The morphology observed from the eight bipolar complexes differs. This group shows a complex activation, resulting from fusion of two waves, that leads to large differences in morphology and amplitude of the bipolar complexes within windows of interest 38. FIG. 2 illustrates ambiguities in detection of activation. The local activation time at which the activation wave passes a point is calculated by locating an event on an electrogram meeting criteria to be described below and subtracting the time of a fiducial point/reference from the time of the event. The time of the reference event may be defined using another intracardiac signal or body surface electrocardiogram.

The inputs to the unipolar annotation algorithm are a single bipolar electrogram and one of its unipolar signals (following signal processing steps to be described below). The unipolar electrograms may be obtained from tip and ring electrodes, which are conventionally positive and negative electrodes, respectively. Alternatively, in some catheters, e.g., spline catheters having multiple tip electrodes and ring electrodes, some of the electrodes may be configured as positive electrodes and others as negative electrodes, wherein any pair of electrodes of whatever type may be chosen for bipolar measurements. References to positive and negative electrodes herein will be understood to include such variants. In the discussion that follows, processing of the bipolar electrogram is described first, followed by a description of unipolar electrogram processing. The unipolar annotation algorithm includes two stages. In the first stage, a time interval, referred to as a window-of-interest is defined. In the second stage, the local activation time is calculated based on characteristics of the unipolar electrogram within the window-of-interest.

Bipolar Electrograms

Figure 3:
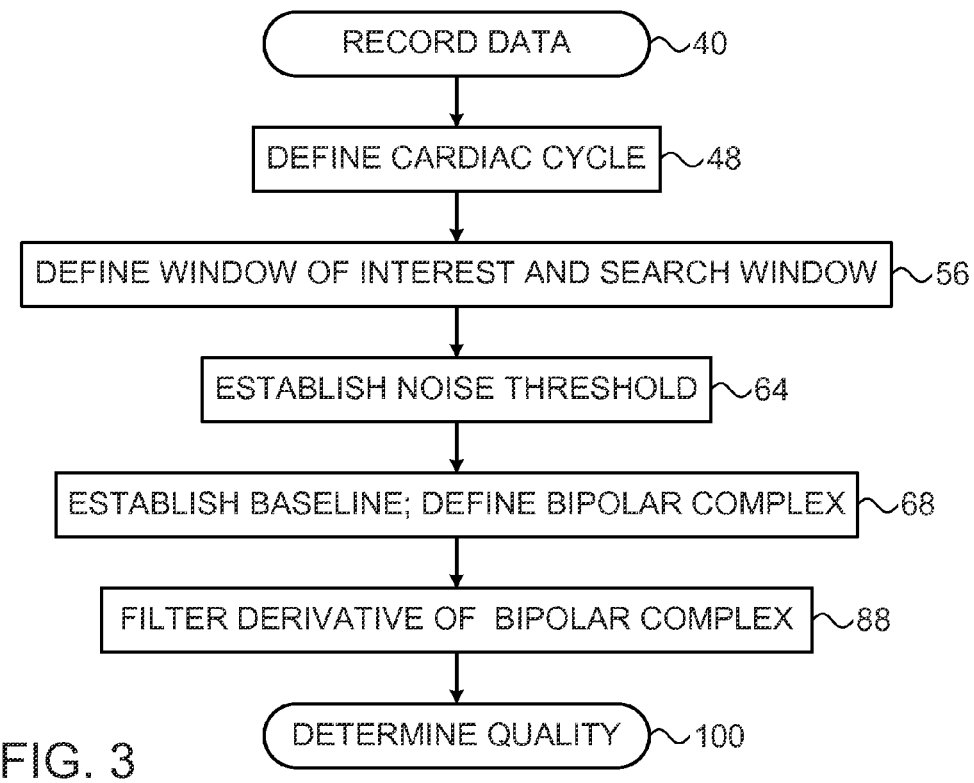
FIG. 3 is a flow chart of a method of activation detection in bipolar electrograms, in accordance with an embodiment of the invention.

Reference is now made to FIG. 3, which is a flow-chart of a method of activation detection in bipolar electrograms, in accordance with an embodiment of the invention. The process steps in this and other flow charts herein are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

At initial step 40 data is acquired. This may consist of 2.5 s of data recording, comprising 2500 samples sampled at 1000 Hz. Alternatively, sampling may be conducted at different rates, e.g. 8000 Hz.

Figure 4:
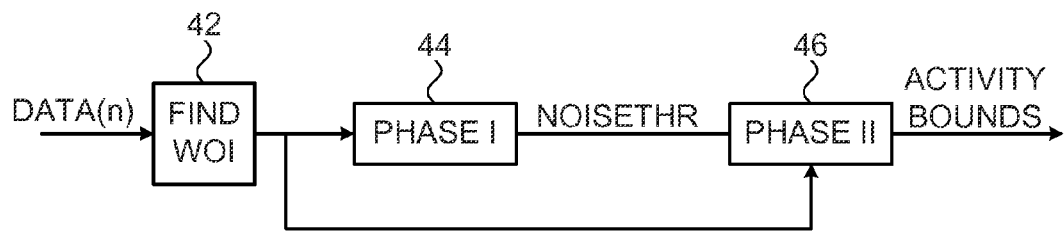
FIG. 4 is a data flow diagram illustrating an embodiment of a portion of the method shown in FIG. 3 in accordance with an embodiment of the invention.

Reference is now made to FIG. 4, which is a high-level data flow diagram illustrating an embodiment of the method using the data obtained in initial step 40 as input. A window-of-interest (WOI) is calculated in block 42, followed by block 44 in which a first phase of the method is completed and by block 46, which represents the second phase.

Reverting to FIG. 3, at step 48 the cardiac cycle is defined. This may be done by detecting the R-wave and differentiating the R-wave detection times. When differentiation is applied to an electrogram, the data series generated indicates a change in voltage (per unit time) rather than the absolute voltage. Therefore, the differentiated electrogram represents the slope of the raw electrogram at any given time point. Other characteristics of an electrogram may be used to define cardiac cycles, as is known in the art.

Figure 5:
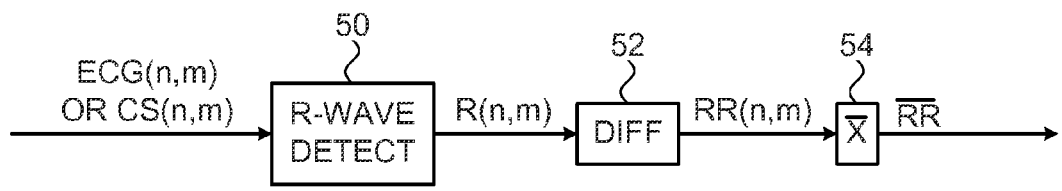
FIG. 5 is a detailed data flow diagram embodying a portion of the method shown in FIG. 3 in accordance with an embodiment of the invention.

Reference is now made to FIG. 5, which is a data flow diagram embodying step 48 (FIG. 3), in accordance with an embodiment of the invention. Analysis of the data obtained in step 48 is conducted in block 50 to detect R-waves. Differentiation is carried out in block 52 to calculate RR-intervals. Then the mean RR-interval is calculated in block 54.

Reverting to FIG. 3, at step 56, configurable parameters for the window-of-interest are assigned: the center ($WOI_{center}$) of the window-of-interest; and the width of a search window (SEARCHWINDOW) and a value A to be applied to the RR-interval. The mean RR-interval and the configurable parameters are used to define the window-of-interest and the search window, the latter being defined by its start ($SW_{start}$) and end ($SW_{end}$). The window-of-interest is defined by its center ($WOI_{center}$) start ($WOI_{start}$) and end ($WOI_{end}$).

Figure 6:
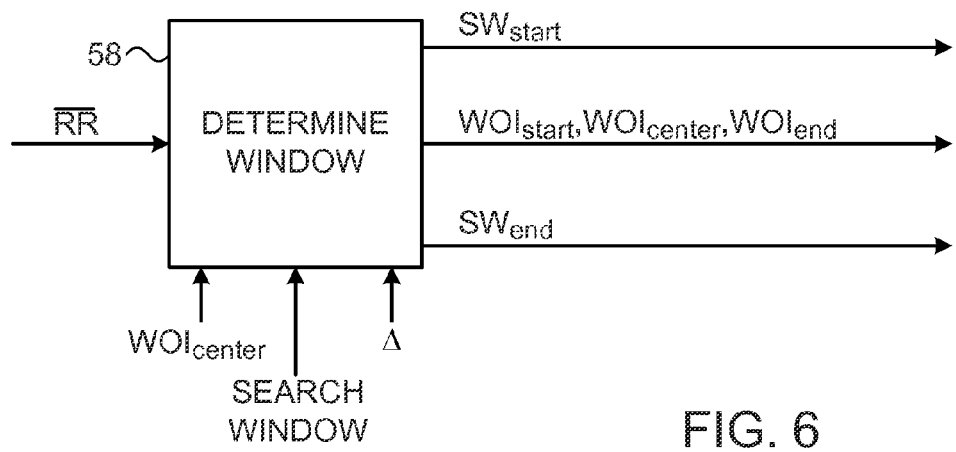
FIG. 6 is a data flow diagram illustrating an embodiment of a portion of the method shown in FIG. 3 in accordance with an embodiment of the invention.

Reference is now made to FIG. 6, which is a data flow diagram embodying step 56 (FIG. 3), in accordance with an embodiment of the invention. Block 58 embodies a function in which the mean RR-interval and the configurable parameters are input, and the values defining the window-of-interest and search window are output. Other descriptors of the cardiac cycle may be utilized in step 56. The actual RR-series and statistics regarding the RR-series, e.g., variance of the RR-interval, may be input in block 58.

Figure 7:
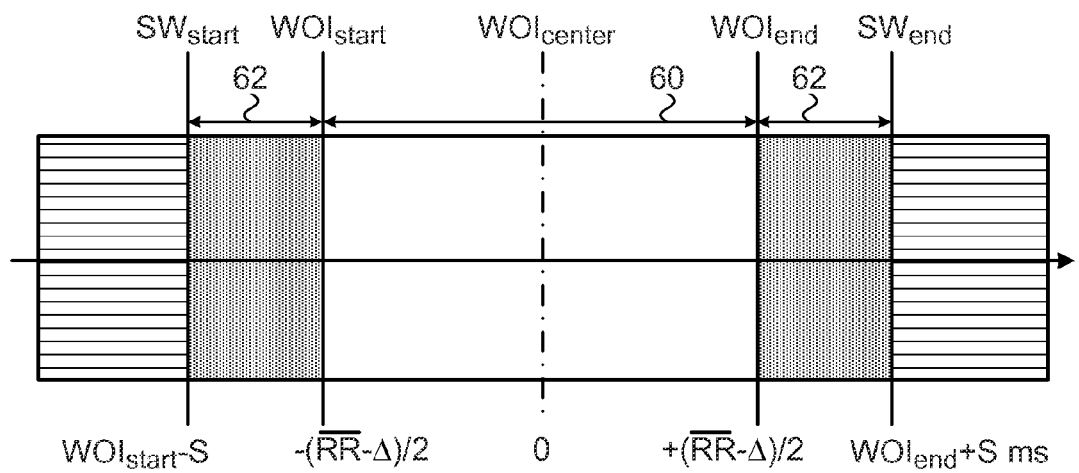
FIG. 7 is an exemplary diagram of a window-of-interest of an electrogram in accordance with an embodiment of the invention.

Reference is now made to FIG. 7, which is an exemplary diagram of a window-of-interest of an electrogram with start and end determined by the mean RR interval, shortened by the value ΔRR/2. An interval represented by arrow 60 defining the window-of-interest is extended by intervals, shown by arrows 62, of a fixed width search window on each side.

Reverting to FIG. 3, the following steps describe the determination of the onset and termination time of the bipolar complex as (shown in FIG. 4). The detection of sharp deflection points in the signal is based on velocity of the signal, and a derivative approach is used. However, derivative functions acts as a high pass filter, thus enhancing high frequency noise. Therefore, a smoothing function is used to decrease the noise in the derivative estimation. The smoothing function is a normalized zero mean Gaussian function with σ=0.9. This function has 90% of the energy in a time window of ±1.5 ms. Thus, activations or approaching far fields in distance larger than this value are virtually ignored and do not affect the derivative value.

At step 64 a noise threshold (NOISETHR) is established, using a low-pass filtered (smoothed) with the baseline-adjusted version of the bipolar electrogram.

At step 68, the low-pass filtered bipolar electrogram is employed in establishing baseline segments (between bipolar complexes). The baseline segments are used to calculate the noise level and demarcate the interval defining the bipolar complex.

Figure 8:
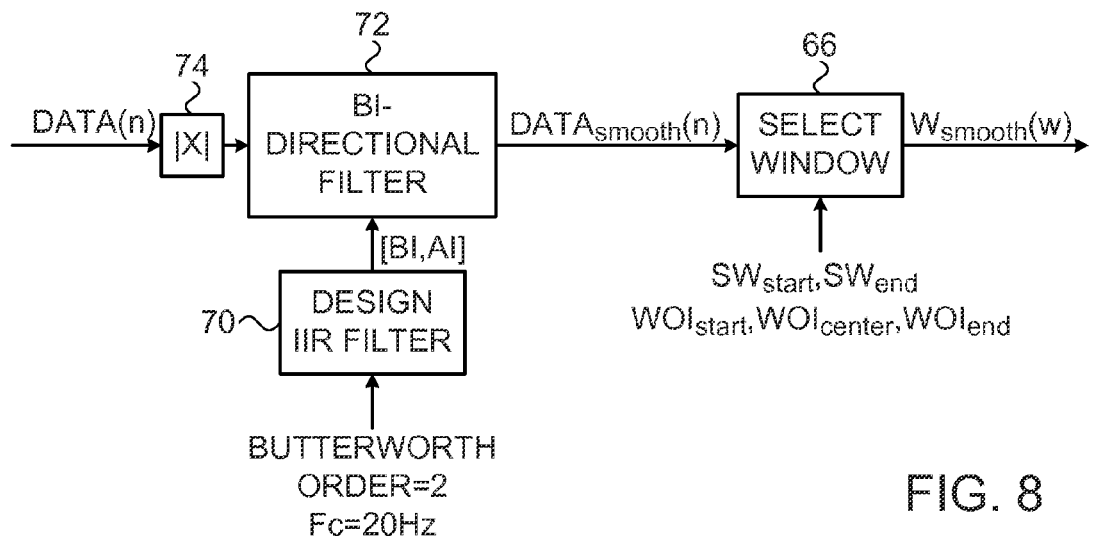
FIG. 8 is a data flow diagram illustrating an embodiment of a portion of the method shown in FIG. 3 in accordance with an embodiment of the invention.

Reference is now made to FIG. 8, which is a data flow diagram embodying a portion of step 64 and step 68 (FIG. 3), in accordance with an embodiment of the invention. A typical design for the low-pass filter is shown in relation to block 70. Filtering of the data occurs in block 72 after absolute values are taken in block 74. A smoothed window version of the window-of-interest and the search window is output in block 66. Optionally, a high pass filter (not shown in FIG. 8) may be included in step 68.

Reference is now made to FIG. 9, which is a data flow diagram embodying a portion of step 68 (FIG. 3), in accordance with an embodiment of the invention. The diagram demonstrates threshold calculation (indicated by block 76) based on the smoothed bipolar electrogram and a two-state machine at block 78 that receives the threshold (SMOOTHR) and the smoothed version of the window-of-interest and search window. The two-state machine reports detection of segments that are used for calculation of the noise threshold in block 46 (FIG. 4) and subsequently to establish local activation onset.

Reference is now made to FIG. 10, which is a schematic diagram illustrating the operation of a state machine 80, represented by block 78 (FIG. 9). In this and in subsequent drawings of state machines, arrows show transitions between states. Necessary conditions and actions are denoted between braces.

The state machine 80 remains in state A 82 so long as the value of data X(n) does not fall below a threshold value (THR). Once a value X(n) falls below the threshold, a transition to state B 84 occurs, and a count is set at zero. Whenever a value X(n) exceeds the threshold, the count is incremented and the machine remains to state B 84. Once the count exceeds a predetermined value (CNTMAX), then a drop in a value X(n) below the threshold causes the machine to transition to state A 82. A smoothed complex 86 is shown in the lower portion of the figure to demonstrate a correlation with the transitions of the state machine 80. Presence of the baseline corresponds to state A 82 and the complex 86 corresponds to state B 84.

In an alternative implementation a segment of data is compared against a threshold and partitioned into sections in which the data is classified as either above or below the threshold. Those sections falling below the threshold and having a duration shorter than a predefined interval, e.g., 8 ms, are ignored. Activation bounds correspond to transitions in the bipolar electrogram from segments showing activity to segments showing no activity.

Reverting to FIG. 3, at step 88, the smoothed bipolar complex is filtered using a FIR filter or an IIR bidirectional filter, differentiated, and a window-of-interest applied.

Figure 11:
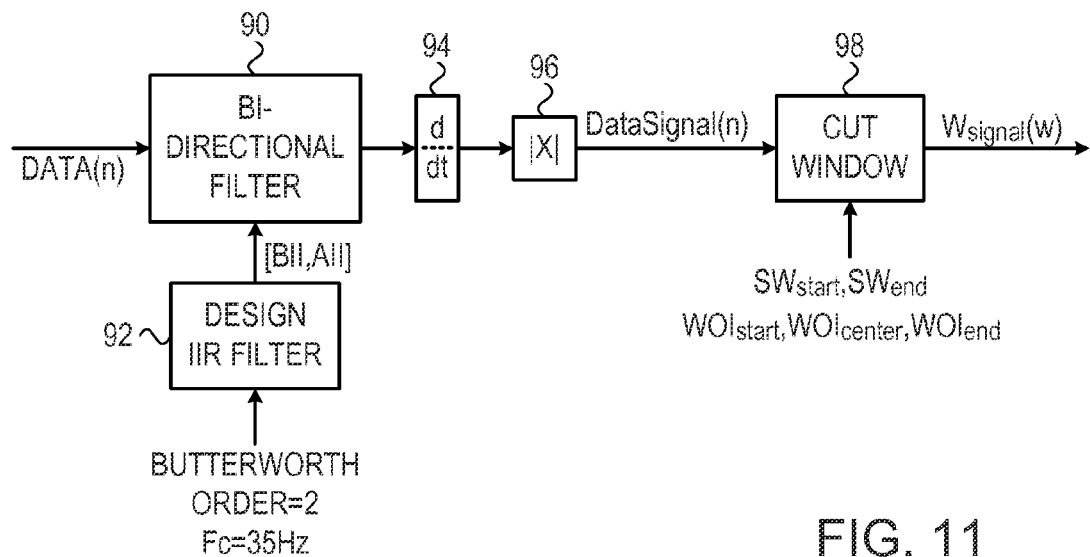
FIG. 11 is a data flow diagram illustrating an embodiment of a portion of the method shown in FIG. 3 in accordance with an embodiment of the invention.

Reference is now made to FIG. 11, which is a data flow diagram embodying step 88 (FIG. 3), in accordance with an embodiment of the invention. Data passes through a bidirectional IIR filter 90, typically a Butterworth filter, whose design is arranged in block 92. Alternatively, a FIR filter, which does not require the use of bidirectional filtering could be used. Differentiation occurs in block 94 followed by conversion to absolute value in block 96. A window-of-interest ($W_{signal}$ (w)) is applied in block 98 to the data output from block 96 (dataSignal(n)).

Reverting to FIG. 3, at final step 100 the quality of the detected onset time point is calculated based on the estimated signal-to-noise ratio (SNR).

Figure 12:
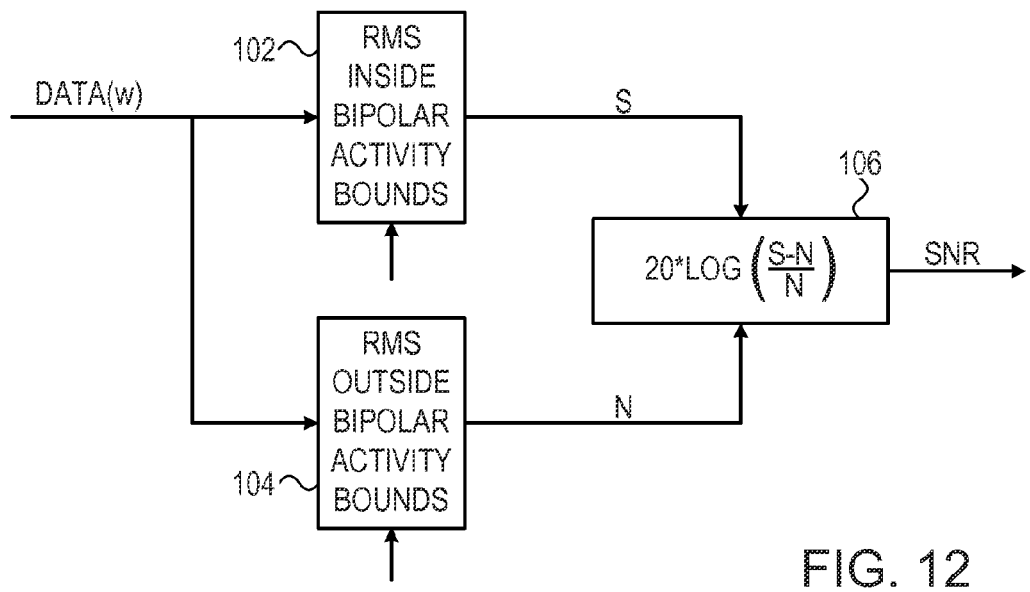
FIG. 12 is a data flow diagram illustrating an embodiment of a portion of the method shown in FIG. 3 in accordance with an embodiment of the invention.

Reference is now made to FIG. 12, which is a data flow diagram embodying an optional aspect of final step 100 (FIG. 3), in accordance with an embodiment of the invention. Root-mean-square (RMS) amplitudes are calculated in block 102 from the signal received within a time window defined by the activity bounds of the bipolar electrogram. Root-mean-square (RMS) amplitudes are calculated in block 104 from the signal received outside the time window, which is treated as noise. The SNR is subsequently calculated as shown in block 106 as a measure of the signal power.

Figure 13:
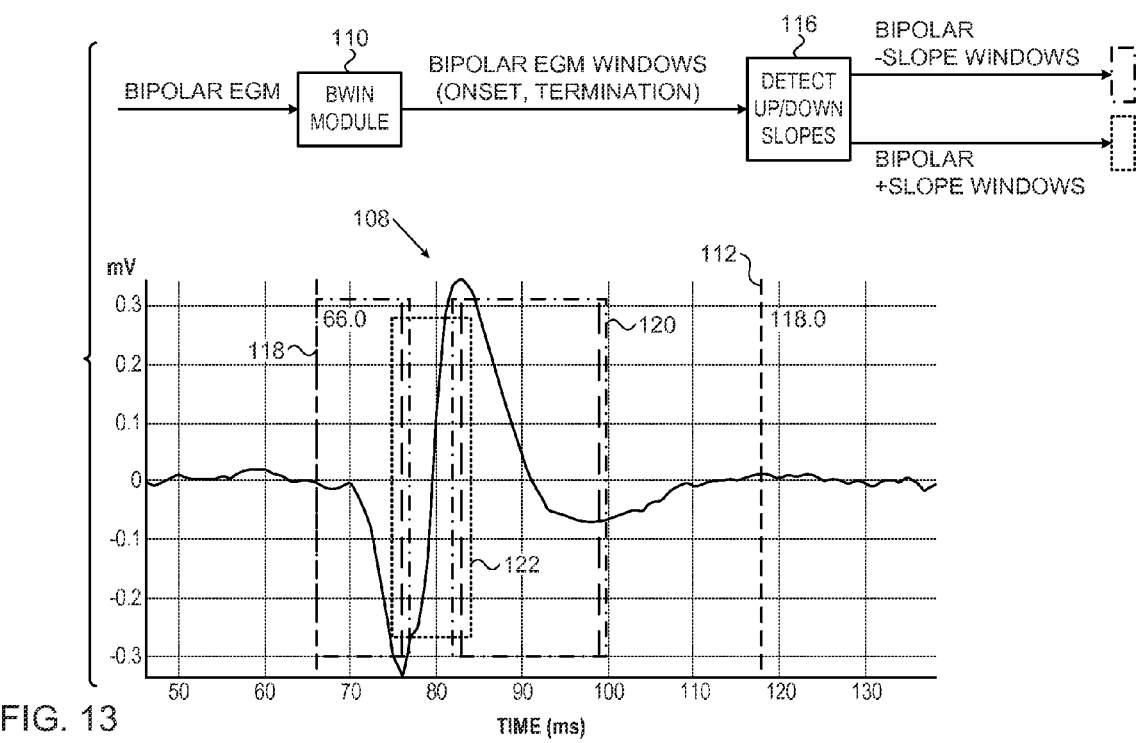
FIG. 13 is a composite figure including a data flow diagram embodying a portion of the method shown in FIG. 27 and a bipolar electrogram tracing in accordance with an embodiment of the invention.

Reference is now made to FIG. 13, which is a composite figure including a data flow diagram for slope detection and a bipolar electrogram tracing 108 in accordance with an embodiment of the invention. The methods described above with reference to FIG. 3 (BWIN Module) are performed in block 110. An interval is defined by lines 112, 114 to encompass the deflection complex in the tracing 108. Positive and negative slopes are detected in block 116. Slope detection is accomplished by analysis of the electrogram signal for minima and maxima.

Windows 118, 120 containing negative slopes and window 122 containing a positive slope are shown in the tracing 108. The windows 118, 120 may be widened, such that a small overlap exists with the window 122.

The windows 118, 120, 122 are treated as bounding intervals for the analysis that follows. Downward sloping intervals in the tracing 108 are identified in the windows 118, 120. A linear regression line is fitted onto each of the downward sloping intervals. If more than one downward sloping interval is found within a window, then their slopes are averaged to compute a trend, and further analysis is conducted as described in further detail below in the description of the hybrid bipolar/unipolar annotation embodiment.

Unipolar Electrograms

Analysis of unipolar electrograms is performed based on the activity bounds obtained from bipolar electrograms using the procedures described below.

Figure 14:
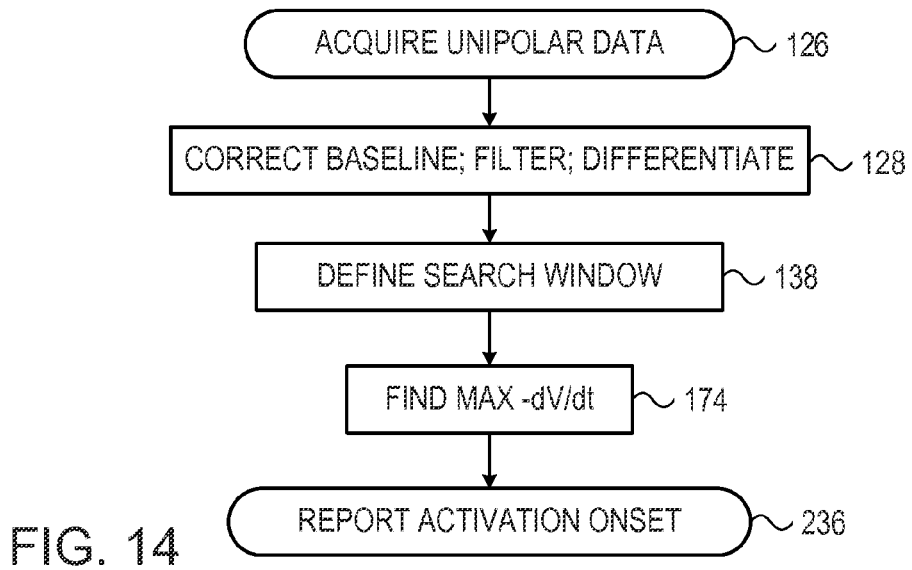
FIG. 14 is a flow chart of a method of activation detection in unipolar electrograms, in accordance with an embodiment of the invention.

Reference is now made to FIG. 14, which is a flow-chart showing details of step 68 (FIG. 3). At initial step 126 data are acquired from an unfiltered unipolar positive and/or negative electrode. For purpose of the description of FIG. 14, it is assumed that bipolar electrogram data have been concurrently acquired from a different set of electrodes The unipolar data may be obtained from one of the bipolar leads.

Next, at step 128, baseline correction, smoothing and differentiation are applied to the unipolar data, using a Gaussian derivative.

Figure 15:
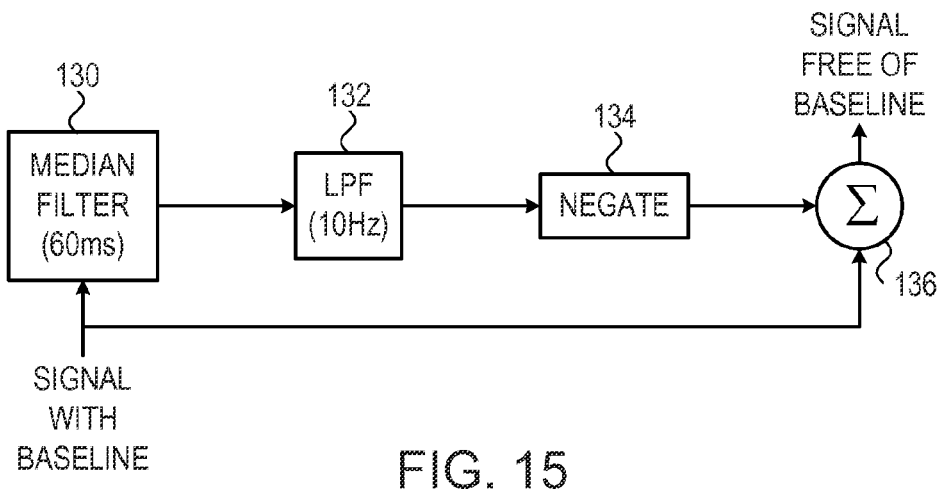
FIG. 15 is a block diagram of a filtering arrangement for baseline correction, in accordance with an embodiment of the invention.

Reference is now made to FIG. 15, which is a block diagram of a filtering arrangement for baseline correction, in accordance with an embodiment of the invention. The filtering arrangement is effective for both unipolar and bipolar electrogram signals, and may be employed to filter data in the hybrid bipolar/unipolar annotation embodiment described below. A median filter 130 is designed to remove the activities from the electrogram signals while a low pass filter 132 (LPF) is designed to smooth out edges resulting from the median filter. Finally in blocks 134, 136 the baseline estimate is subtracted from the raw signal resulting in a signal free of baseline.

Figure 16:
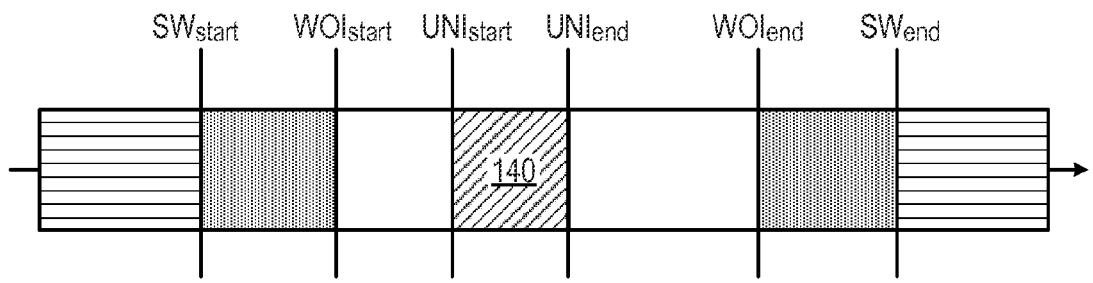
FIG. 16 is a diagram illustrating a search window illustrating a search window in accordance with an embodiment of the invention.

Reverting to FIG. 14, at step 138 a time interval for a search window is defined. Reference is now made to FIG. 16, which is a diagram illustrating a search window for unipolar data, based on an interval 140 between unipolar activity bounds of a filtered differentiated unipolar electrogram complex ($W_{signal}$), in accordance with an embodiment of the invention.

Figure 17:
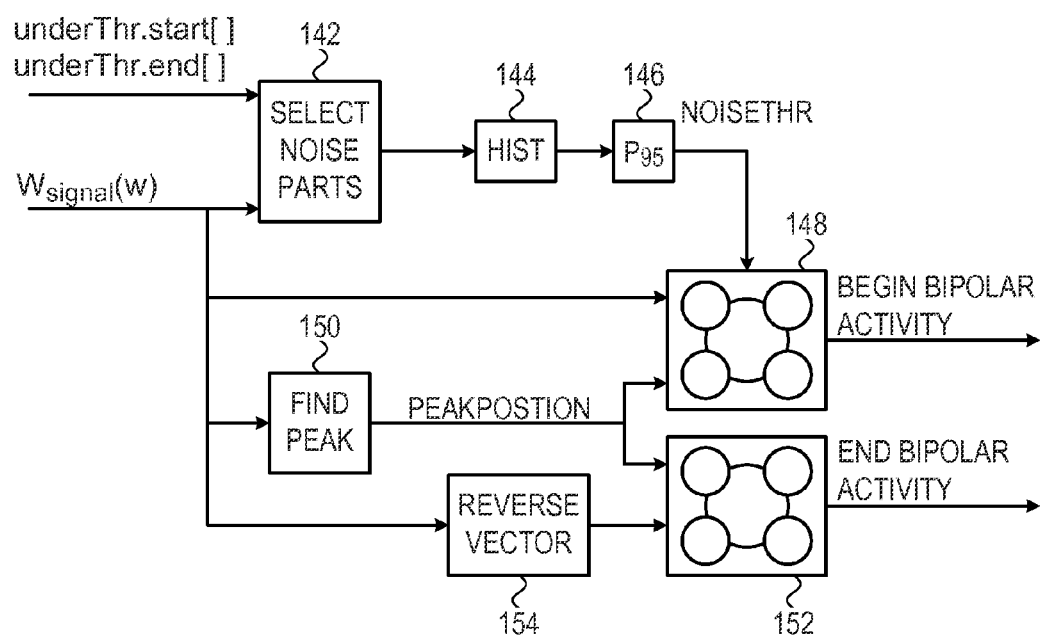
FIG. 17 is a data flow diagram illustrating an embodiment of a portion of the method shown in FIG. 3 in accordance with an embodiment of the invention.

Reference is now made to FIG. 17, which is a data flow diagram embodying step 138 (FIG. 14), in accordance with an embodiment of the invention. Amplitude of the data is determined in blocks 142, 144, 146 and a signal comparing the amplitude to the noise threshold is provided to a state machine 148. Peak detection within the window-of-interest is performed in block 150, and the position of the peak reported to state machines 148, 152. State machines 148, 152 operate in the same manner. State machine 148 is controlled by the filtered bipolar electrogram to find the local activation time. State machine 152 uses a time-reversed version of the filtered bipolar electrogram to determine the local termination time. The reversed version is prepared in block 154.

Figure 18:
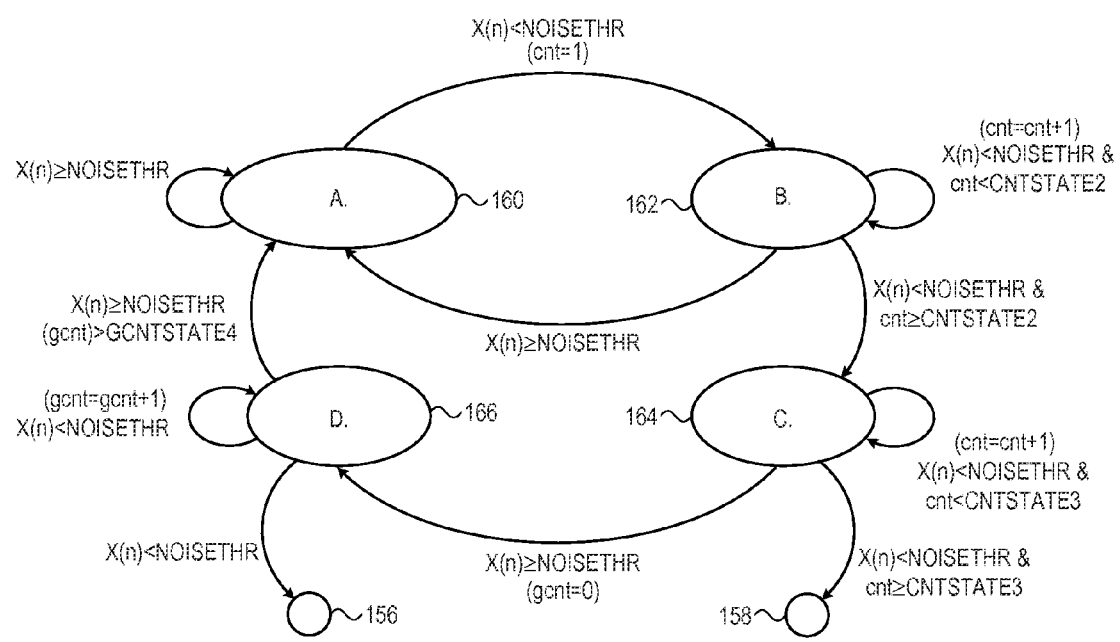
FIG. 18 is a schematic diagram illustrating the operation of state machines shown in FIG. 17.

Reference is now made to FIG. 18, which is a schematic diagram illustrating the operation of the state machines 148, 152 (FIG. 17), in accordance with an embodiment of the invention. The conventions of FIG. 10 are followed in FIG. 18. Additionally, small circles 156, 158 denote exit states. Starting at the peak of the bipolar complex determined in block 150 (FIG. 17), the state machine is started at state A 160, while searching backward in time. While the amplitude of the filtered bipolar complex stays above the noise threshold (NOISETHR), state A 160 is maintained. When the amplitude value X(n) falls below the noise threshold, the state machine moves from state A 160 to state B 162 and a counter (cnt) is set to 1.

While the machine is in state B 162, if at any time the value X(n) is no longer below the noise threshold the machine returns to state A 160. However, so long as the value X(n) is below the noise threshold, state B 162 is maintained and the counter cnt increments. When the counter cnt reaches a predetermined value (CNTSTATE2), a transition to state C 164 occurs provided that the value X(n) does not exceed the noise threshold.

In state C 164, if at any time the value X(n) is no longer below the noise threshold the machine transitions to state D 166, and another counter (gcnt) is set to 0. However, so long as the value X(n) is below the noise threshold, state C 164 is maintained and the counter cnt increments. When the counter cnt reaches a predetermined value (CNTSTATE3), a transition to the exit state indicated by circle 158 occurs.

In state D 166 if at any time the value X(n) falls below the noise threshold the machine transitions to the exit state indicated by circle 156. This exit state marks the end of the activation segment. However, so long as the value X(n) is below the noise threshold, the counter gcnt increments. When the counter gcnt exceeds a predetermined value (CNTSTATE4), a transition to state A 160 provided that the value X(n) still reaches or exceeds the noise threshold.

Figure 19:
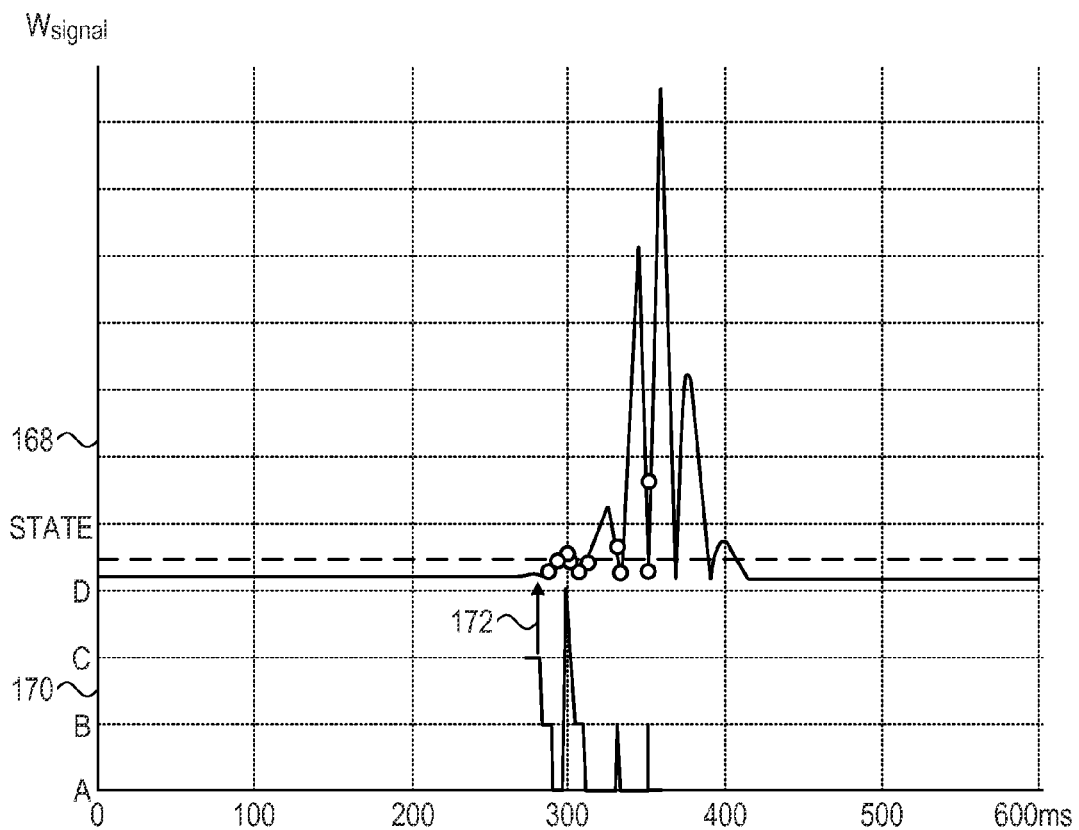
FIG. 19 is a composite tracing illustrating an exemplary operation of the state machine of FIG. 18.

Reference is now made to FIG. 19, which is a composite tracing illustrating an exemplary operation of the state machine shown in FIG. 18. A bipolar electrical complex is shown in in upper pane 168 opposing a plot in lower pane 170 of the state transitions of the state machine, in accordance with an embodiment of the invention. State machine states begin at the peak position of the filtered bipolar complex moving backwards in time while moving between state A 160 (FIG. 18) and state B 162, eventually reaching an exit state (detection) (indicated by arrow 172) when emerging from state C 164. It will be recalled from the discussion regarding FIG. 10 that the use of the state machine can be replaced by classification of segments of the data.

Reverting to FIG. 14, next, at step 174 the interval 140 (FIG. 16) is searched to find the maximum negative values of dV/dt (−dV/dt) based on an unfiltered unipolar (positive and/or negative) electrogram.

Figure 20:
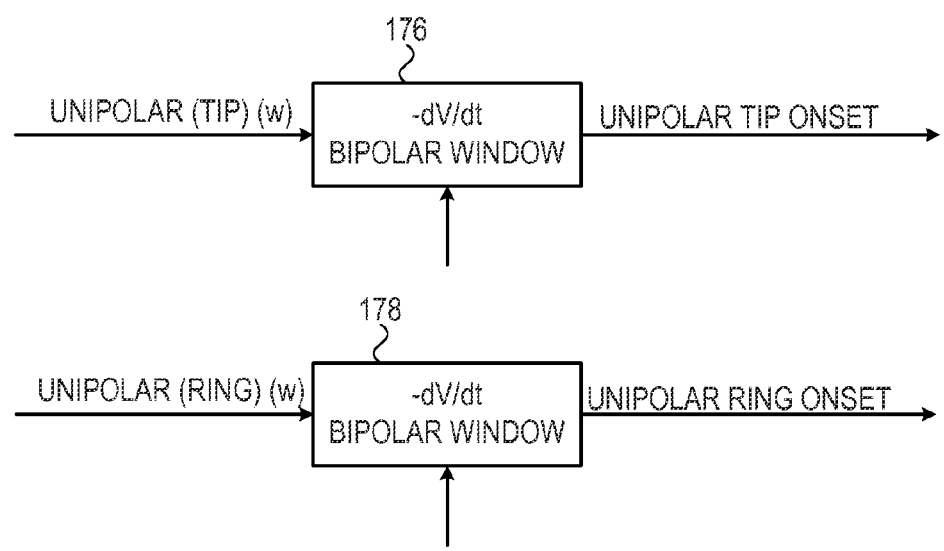
FIG. 20 is a data flow diagram illustrating an embodiment of a portion of the method shown in FIG. 14 in accordance with an embodiment of the invention.

Reference is now made to FIG. 20, which is a data flow diagram embodying step 174 (FIG. 14), in accordance with an embodiment of the invention. Cases are shown in blocks 176, 178 respectively for ring and tip (negative and positive) electrodes, which can co-exist on the distal segment of a cardiac catheter. The unipolar electrograms are searched between specified boundaries, e.g., interval 140 (FIG. 16).

Figure 21:
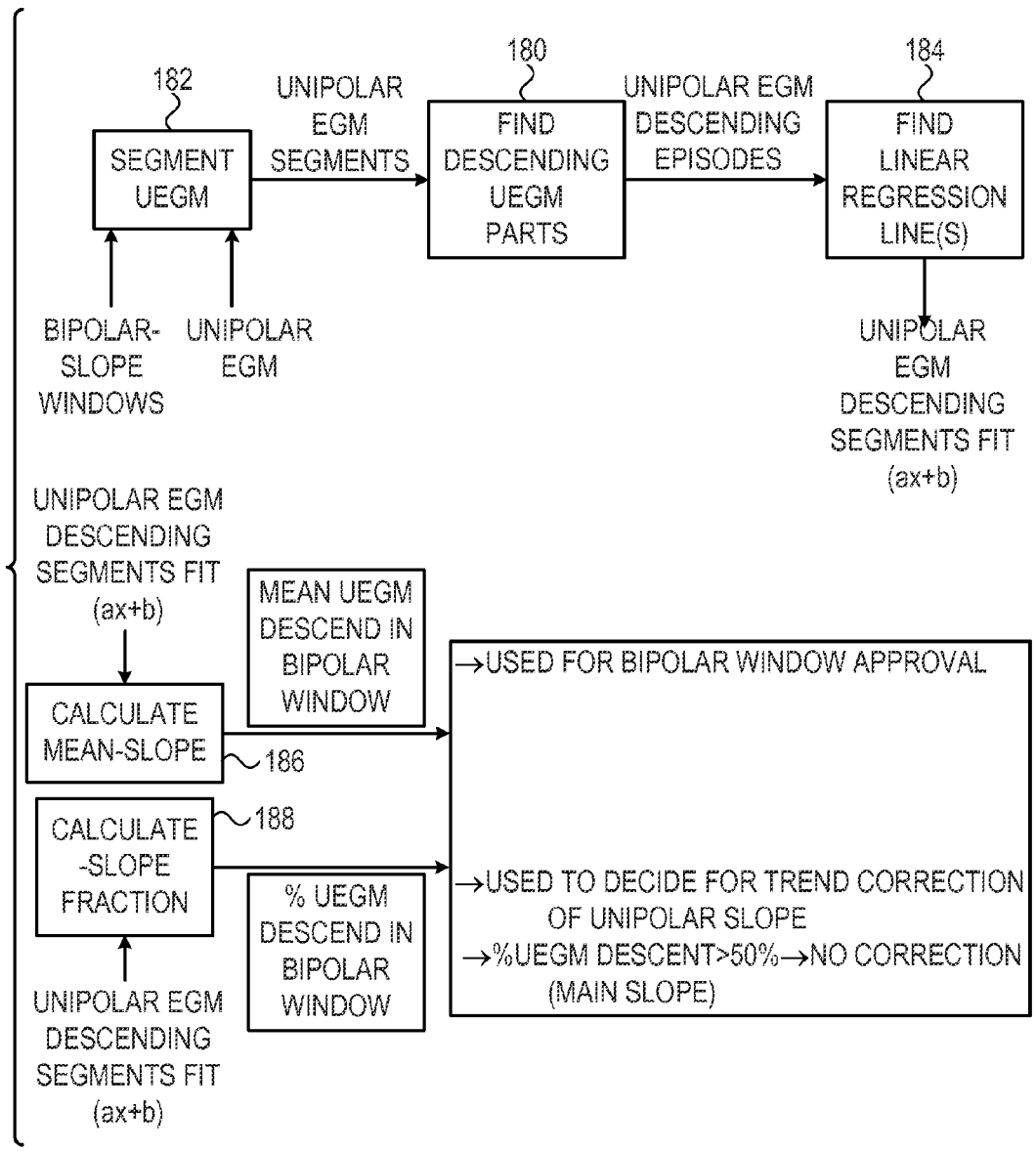
FIG. 21 is a data flow diagram embodying a portion of the process of FIG. 27, in accordance with an embodiment of the invention.

Reference is now made to FIG. 21, which is a data flow diagram embodying a portion of step 174 (FIG. 14), in accordance with an embodiment of the invention. In blocks 180, 182 downward sloping intervals corresponding to downward slopes in the associated bipolar electrogram are detected as described above in the description of FIG. 13. In block 184 respective linear regression lines are fitted to the downward sloping intervals. In block 186 a mean trend is determined from an interval encompassing all the downsloping segments in the window under consideration. This is used as another decisional criterion for approval of the annotation. In block 188 the fraction of the longest monotonic segment within the unipolar slope window relative to the duration of the entire slope segment that is occupied by each of the unipolar slopes is calculated. The output of block 188 is used to determine whether to adjust the slope (−dV/dt) of detected segments in the unipolar electrogram as described below according to the trend calculated in block 186.

Figure 22:
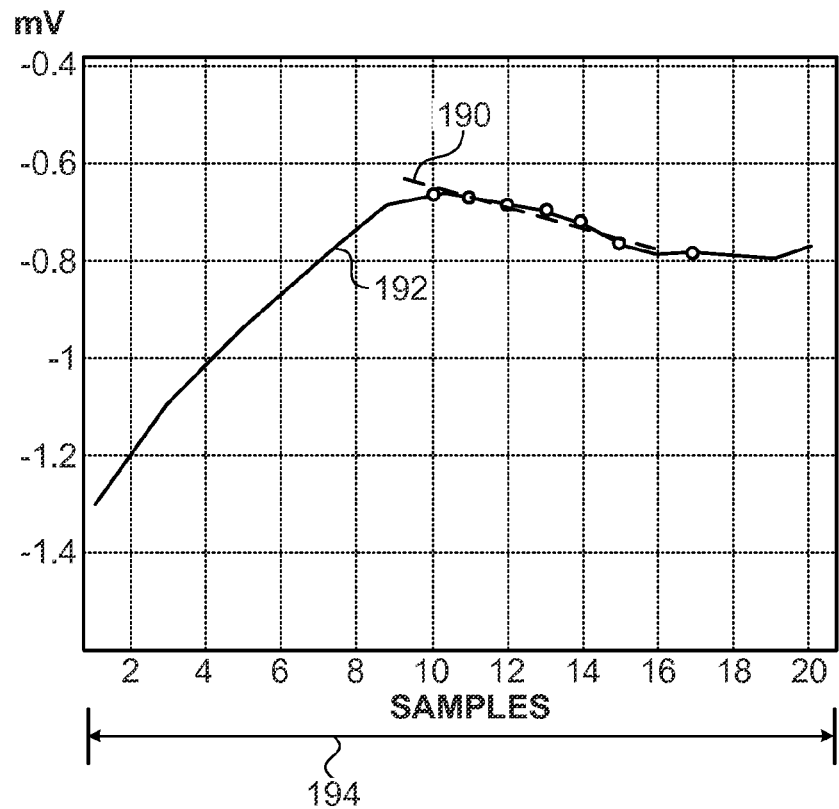
FIG. 22 is a graph illustrating the operation of the data flow shown in FIG. 21, in accordance with an embodiment of the invention.

Reference is now made to FIG. 22, which is a graph illustrating the operation of the data flow shown in FIG. 21, in accordance with an embodiment of the invention. A line 190 has been fitted to a monotonic downsloping segment of a unipolar electrogram tracing 192 within a window 194 that relates to bipolar electrogram activity (not shown). The segment has a slope of −0.29 and occupies 30% of the window.

Figure 23:
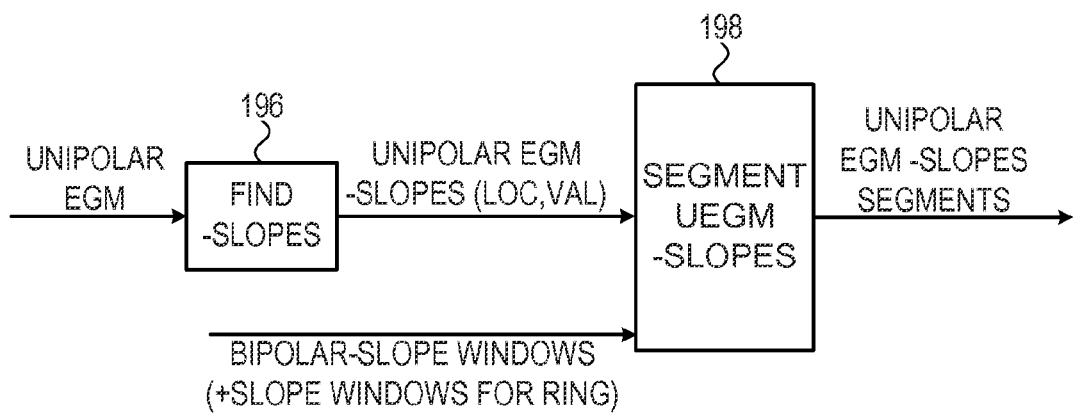
FIG. 23 is a data flow diagram embodying a portion of the process of FIG. 27, in accordance with an embodiment of the invention.

Reference is now made to FIG. 23, which is a data flow diagram illustrating segmentation of a unipolar electrogram tracing having negative slopes, in accordance with an embodiment of the invention. Portions of the tracing having negative slopes are identified in block 196. Slopes falling within the slope windows of bipolar tracings are correlated. Identification of the segments is accomplished in block 198.

Superposition of a detected unipolar downward sloping interval onto a wider interval having an upward slope would lead to underestimation of the detected slope. Alternatively, if a detected downward sloping interval were superimposed on a wider downward slope, it would lead to overestimation of the detected slope. In both situations, a correction needs to be made when the detected unipolar downward sloping interval covers a limited percentage (≤50%) of the total width of a bipolar window. This percentage can be varied, e.g., based on electrode types and characteristics.

Figure 24:
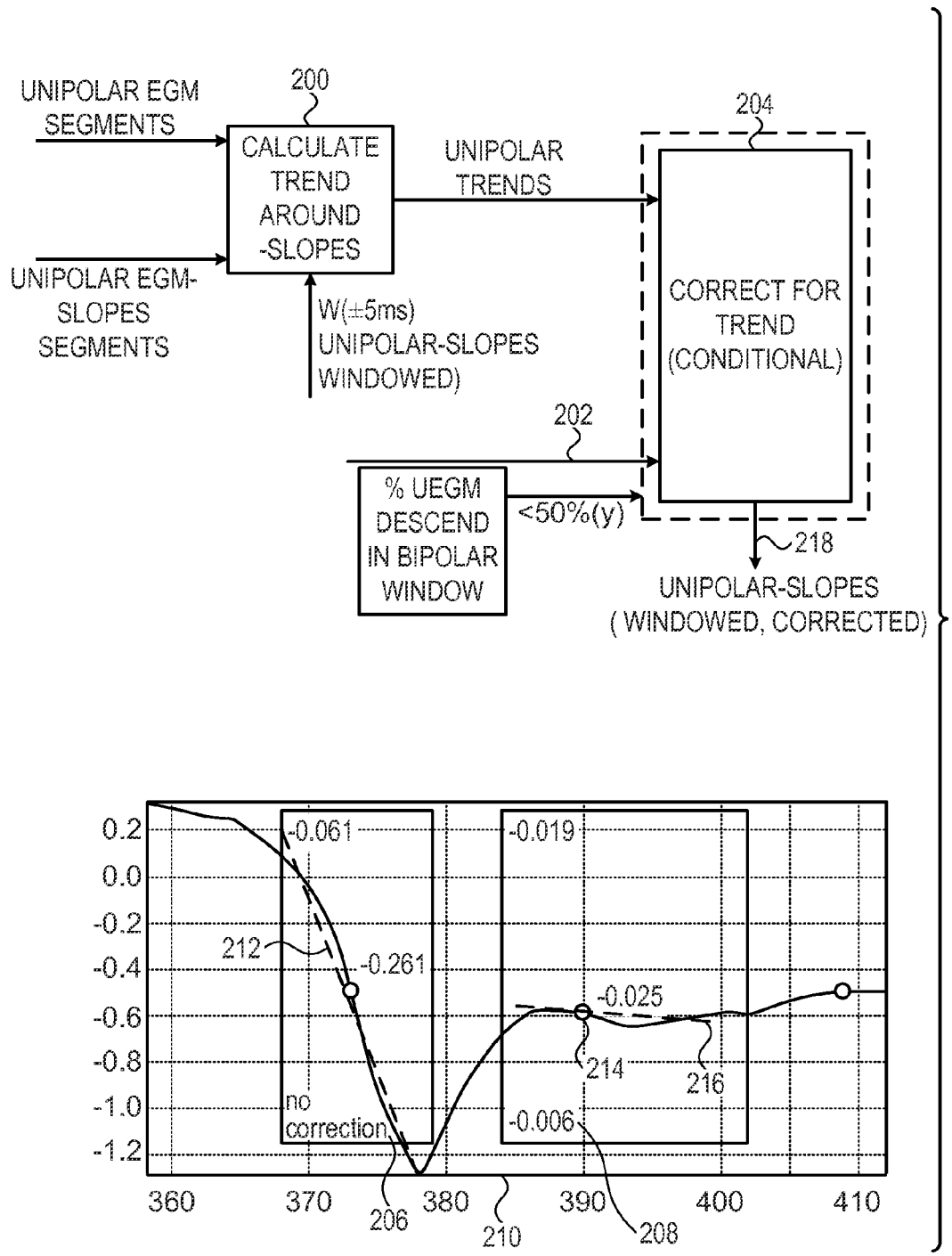
FIG. 24 is a data flow diagram embodying a portion of the process of FIG. 27, in accordance with an embodiment of the invention.

Reference is now made to FIG. 24, which is a data flow diagram embodying a portion of step 174 (FIG. 14), in accordance with an embodiment of the invention. In block 200 the trend around the negative unipolar electrogram slopes is calculated by averaging the slopes of all downward sloping intervals within the relevant window-of-interest. Then the output of block 200, and block 188 (FIG. 22) and the trend within the unipolar slope windows (shown as arrow 202) are submitted to block 204 where the slopes of unipolar electrogram segments may be adjusted. Two bipolar electrogram slope windows 206, 208 are illustrated in tracing 210. Correction is applied to a downward sloping interval if it occupies less than 50% than its containing bipolar window. An interval having a steep monotonic downward slope 212 (−0.261 mV/ms) extending from 367 ms to 378 ms covers more than 50% of the window 206. From this it is concluded that this slope need not be corrected. A less steep monotonically sloping segment of the tracing having slope 214 occupies less than 50% of the window 208 and is corrected by subtracting the slope of the trend in the window 208 (shown as broken line 216) from the value of dV/dt. Block 204 generates output 218 consisting of adjusted slopes in the unipolar electrogram.

Figure 25:
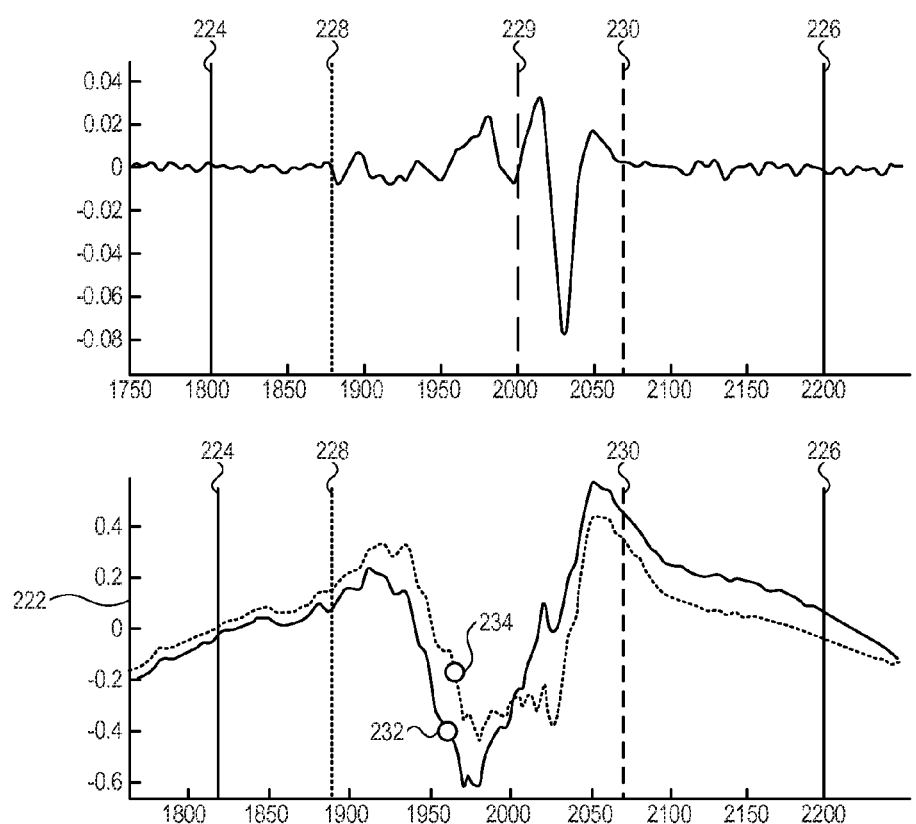
FIG. 25 is a graphical example illustrating onset detection in unipolar electrograms in accordance with an embodiment of the invention.

Reference is now made to FIG. 25, which is a graphical example illustrating activation onset detection in unipolar electrograms in accordance with an embodiment of the invention. Bipolar and unipolar electrogram signals are shown in an upper panel 220 and lower panel 222 respectively, The solid lines 224, 226 define a user-configurable window-of-interest, which is generally not identical to the window of interest for the bipolar electrogram shown in FIG. 7. The bipolar activity bounds are shown as dashed lines 228, 230. Unipolar activation detection points 232, 234 indicate the maximum negative slope (−dV/dt) and are compared to a reference time indicated by line 229. In this example the points 232, 234 occur earlier than the reference time.

Reverting to FIG. 14, the times corresponding to points 232, 234 (FIG. 25) and reported as the unipolar activation onset in final step 236.

Hybrid Bipolar/Unipolar Annotation Embodiment

In this embodiment, the procedures described above with reference to FIG. 3 and FIG. 14 are extended. The procedures in this embodiment utilize smoothed baseline-removed derivatives of bipolar electrograms and unipolar electrograms. They operate automatically and continuously on electrode signal data. Times corresponding to deflections (minima) in the derivative signal of the unipolar signals are tentatively marked as annotations. All such deflections are initially considered to maximize sensitivity; however only those deflections showing correlated activity in the bipolar electrogram are retained.

The bipolar electrogram is a record of the difference between two unipolar electrograms (M1−M2). Essentially all possibly significant downward deflections in at least one of the two unipolar electrograms are detected, and those deflections having a derivative (−dV/dt) below a specific threshold are further analyzed. Deflections having a low bipolar-to-unipolar synchronicity score, i.e., lacking significant correlation with activity in the bipolar electrogram, are rejected. Such non-correlating unipolar activity can occur, e.g., due to magnetic field interferences such as may be caused by fluoroscope detectors and collimators, power line effects, and far field activity of the ventricle. The last can occur, e.g., in supraventricular tachycardia.

In practice both unipolar and bipolar electrogram signals may contain additive baseline wander signals arising from movement of the catheter, movement of the subject and respiration that changes the interface with the tissue. These motion artifacts contain mostly low frequency components. However, the near field activity signal may also contain significant energy in this spectral band. The conventional approach of removal by high pass IIR or FIR filter is problematic, and can cause distortion and morphology changes to the raw signals. Therefore, the approach employed is based on estimation of the baseline wander and its subtraction from the electrogram signal. This may be accomplished by removal of the near field activity using the filtering arrangement described above with respect to FIG. 15.

Reference is now made to FIG. 26, which is a graph illustrating separation between local activation and far field activity based on correlated and uncorrelated electrical activities in bipolar and unipolar electrograms, in accordance with an embodiment of the invention. Examination of the unipolar and bipolar derivatives shows correlated and uncorrelated activity in windows 238, 240, respectively.

An advantage of this embodiment is its ability to detect and eliminate far field signals, which can generate sharp deflections. Another advantage is the consideration of all possible qualified deflections (referred to herein as "annotations"). Some of these deflections may be missed by conventional techniques, particularly at the edges of windows-of-interest.

Reference is now made to FIG. 27, which is a flow-chart of a method of activation detection in unipolar and bipolar electrograms, in accordance with an alternate embodiment of the invention. At initial step 242 unipolar and bipolar electrogram electrograms are acquired.

In a preprocessing phase 244 the unipolar signal and the bipolar electrogram signals are filtered, adjusted to null their baselines, and a smoothed derivative calculated. In step 246 the unipolar electrogram data local minima (−dV/dt) in a differentiated unipolar electrogram of a unipolar electrogram below a threshold are detected.

Next, an annotation phase 248 begins, which includes steps 250, 252, 254, 256, 258. Unipolar electrogram slopes and bipolar electrogram slopes are calculated in steps 254, 256, respectively. In step 250 the local minima detected in step 246 are correlated with the differentiated bipolar electrogram, and minima in the unipolar and bipolar derivative electrograms that are consistent with the slopes of the bipolar electrogram are selected. Candidate annotation points are unipolar local minima are evaluated against at least the following criterion:

(1) The amplitude of the bipolar smoothed derivative signal in a time window around the candidate annotation points (±2 ms) must not exceed −0.008 mV/ms.

Combinations and subcombinations of additional criteria are optionally imposed against the candidate annotation points:

(2) The value of the slope of the unipolar electrogram at the candidate annotation point is below −0.01 mV/ms.

(3) The peak-to-peak value of an activity in a unipolar and/or bipolar electrogram that includes a candidate annotation point is above specific amplitude (typical 0.003-0.008 mV). For this purpose, the peak-to-peak value is the maximum excursion of the signal in the activity that includes the candidate annotation point.

(4) the bipolar/unipolar slope ratio is greater than 0.2. For this purpose the value of a negative electrode is inverted.

Criterion (1) is evaluated in step 258. Criteria (2)-(4) are evaluated in step 252. The values of the criteria given above are exemplary, and may be varied for a given patient or medical condition. Additional optional criteria include local trend and signal morphology.

The above-noted ratio between the slopes of the unipolar and the bipolar electrogram signals measured at a candidate annotation point is useful as a classification criterion since this ratio can differentiate between near field and far field activity. In near field activity at least some of the downslope activity should be represented in the bipolar signal, while in far field cases the bipolar electrogram will have only residual activity. Alternatively, other methods known in the art may be employed to assess associations between the unipolar and the bipolar electrogram signals. For example, various correlation coefficients can be calculated. Additionally or alternatively, covariance matrices, and tests of statistical significance may be used to assess the relationships of the two electrograms.

The bipolar derivative value at a candidate annotation point is computed differently for positive and negative electrodes. For positive electrode it is the minimal value within the time window (±2 ms) and for negative electrode it is the negative value of the maximal value within that time window. The reason for using a time window is that in certain pathologies and/or orientations (catheter and wave propagation direction) the bipolar signal at a given point can be small or even zero since the time delay of activities between unipolar activations can cancel out. The value is calculated differently for positive and negative electrodes since the tip activity is registered as downslope in the bipolar while activity in the negative electrode is registered as an upslope in the bipolar signal.

Figure 28:
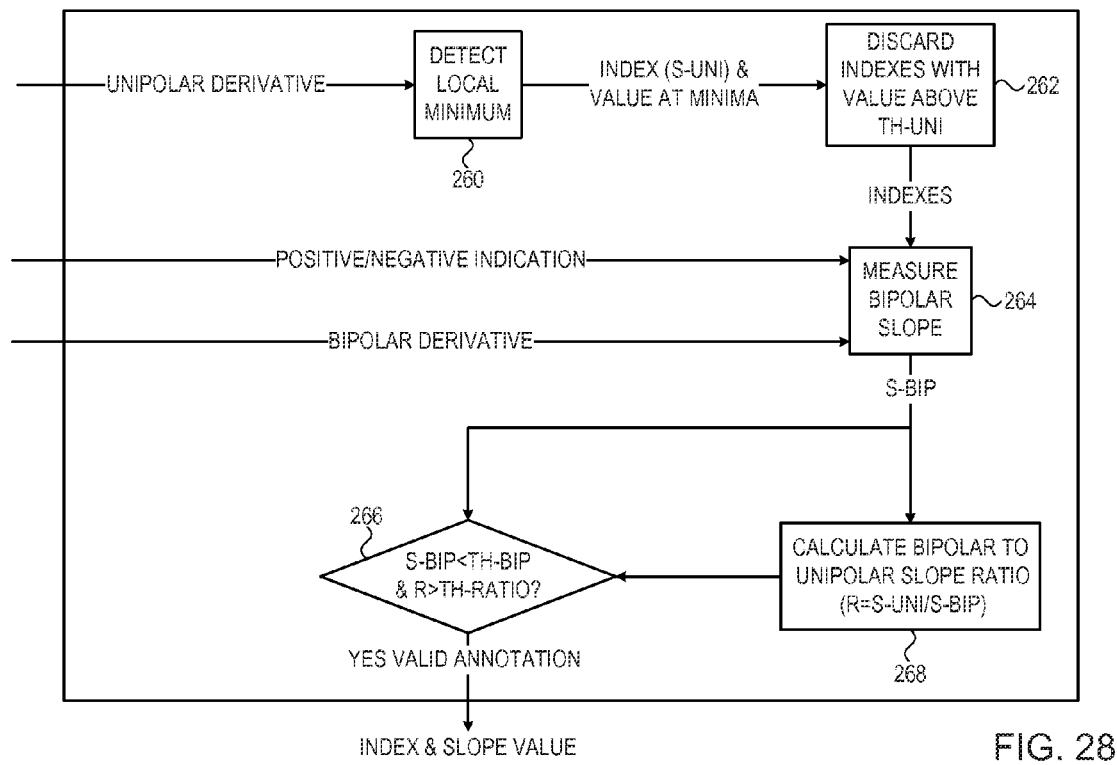
FIG. 28 is a data flow diagram illustrating an embodiment of a portion of the method shown in FIG. 27 in accordance with an embodiment of the invention.

Reference is now made to FIG. 28, which is a data flow diagram embodying phase 248 (FIG. 27), in accordance with an embodiment of the invention. The inputs to the block are the smoothed derivative of the unipolar electrogram under test, its polarity and its corresponding bipolar electrogram. At block 260 local minima are detected in the smoothed derivative of the unipolar electrogram. Minima with deflection stronger than the minimal deflection rate are identified in block 262 are further evaluated for bipolar slope in block 264.

Finally, the consistency of the slope is evaluated at decision block 266 using a ratio test that is determined in block 268. Valid annotations are those meeting the above-noted criteria.

Figure 29:
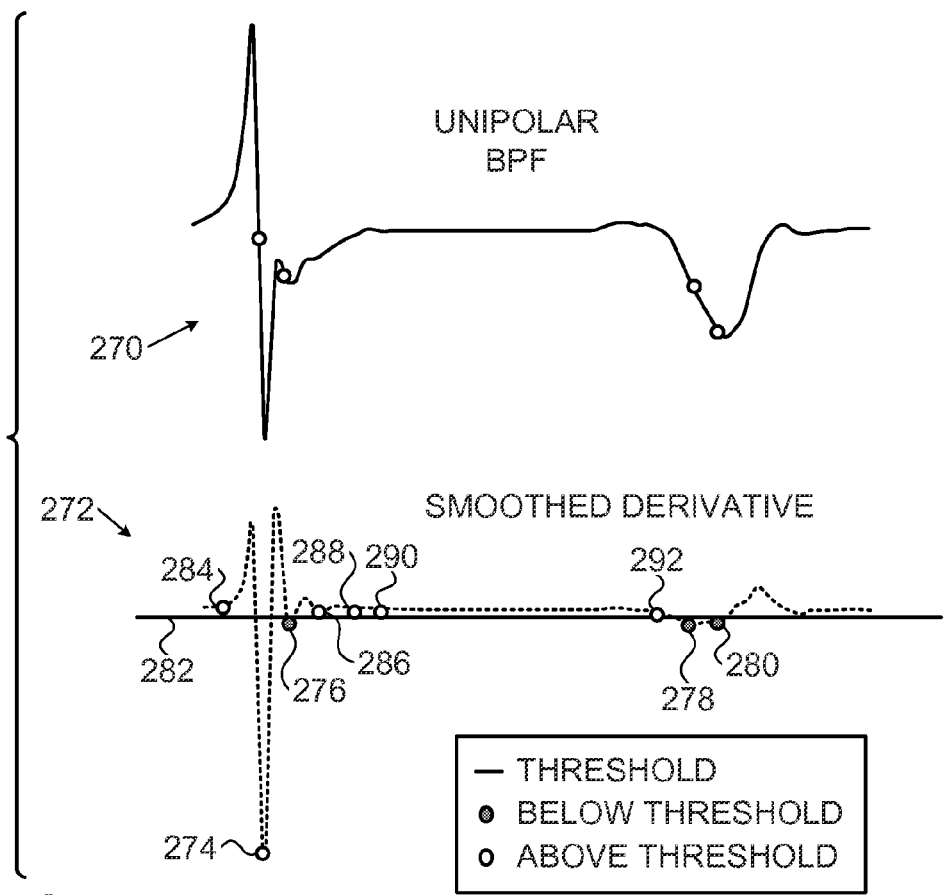
FIG. 29 is a graphic illustration of a portion of an annotation procedure, in accordance with an embodiment of the invention.

Reference is now made to FIG. 29, which is a graphic illustration of a first phase of an annotation procedure, in accordance with an embodiment of the invention. A unipolar electrogram tracing 270 and its smoothed derivative 272 are shown. Points 274, 276, 278, 280 are minima in the derivative signal below threshold value, (horizontal line 282) and will be further considered as possible annotation points. Points 284, 286, 288, 290, 292 mark minima above the threshold that will be rejected.

Figure 30:
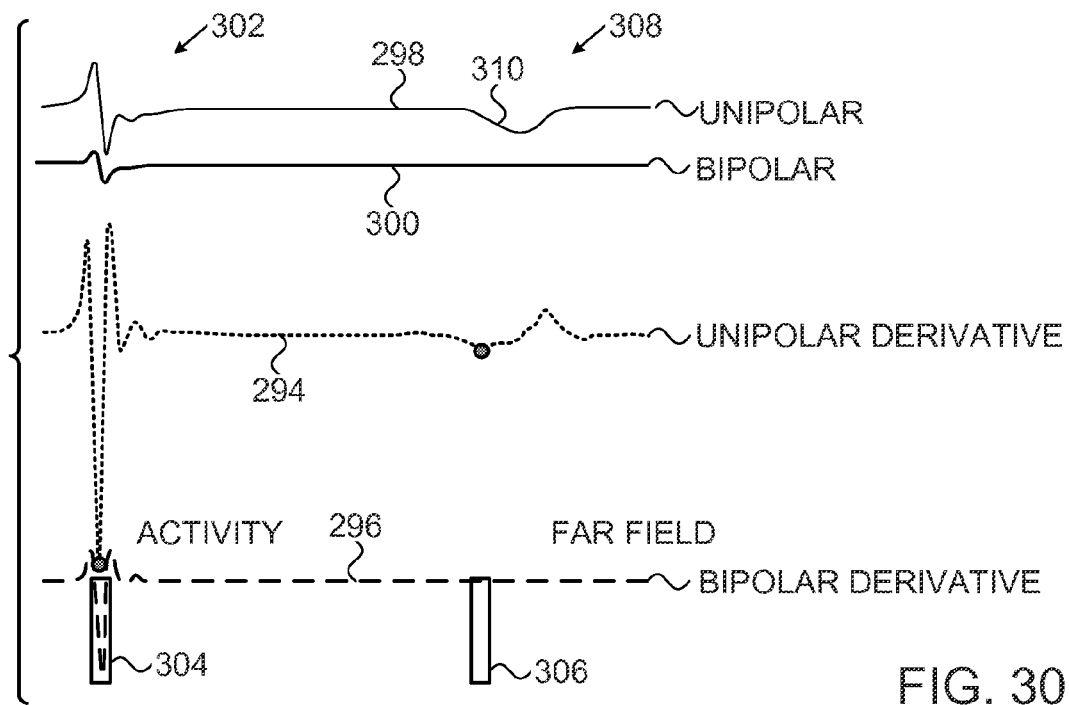
FIG. 30 is a graphic illustration of another portion of an annotation procedure, in accordance with an embodiment of the invention.

Reference is now made to FIG. 30, which is a graphic illustrating phase 248 (FIG. 27), in accordance with an embodiment of the invention. Derivatives 294, 296 of a unipolar electrogram 298 and a bipolar electrogram 300, respectively are used for calculating the bipolar slope change and the ratio between them. When near field activity 302 exists in the unipolar signal, there is also activity in the bipolar signal (derivative 296) within a time window 304, ±2 ms around a deflection point. However, this is not the case of time window 306 in the case of far field activity 308, For activity 308 the bipolar/unipolar slope ratio will be below threshold and a candidate annotation point 310 would be rejected in block 266 (FIG. 28).

Figure 31:
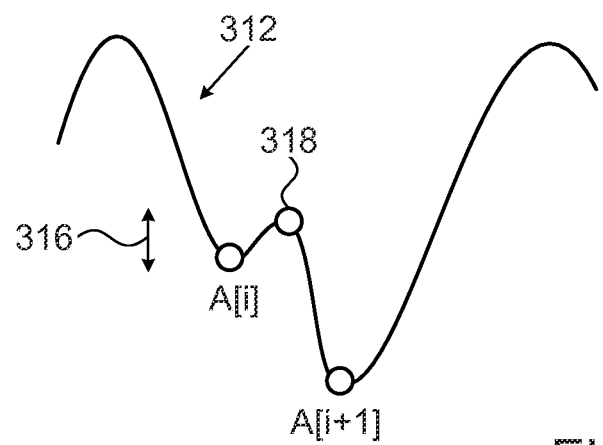
FIG. 31 is a tracing of a derivative signal from a unipolar electrogram, illustrating identification of a single activity, in accordance with an embodiment of the invention.

Reference is now made to FIG. 31, which is a tracing 312 of a derivative signal from a unipolar electrogram, illustrating identification of a single activity, in accordance with an embodiment of the invention. The unipolar derivative signal and two possible annotations marked A[i] and A[i+1]). One aspect of step 314 (FIG. 27) is to decide whether an upsloping amplitude change (marked by vertical arrow 316) is significant or not. A single activity is exemplified in FIG. 31 when:

(1) the ratio between peak 318(P) minus activation A[i] relative to A[i] is larger than a predefined value, typically 0.5:

$$(P-A[i])/A[i] > 0.5, \text{ and}$$

(2) the change in the signal amplitude (P−A[i]) is at least 0.01 mV. If both criteria are met both annotations A[i] and A[i+1] are maintained. Otherwise the weaker activation A[i]) is discarded.

Reverting to FIG. 27, at a post-processing step 314 annotations arising from a single activity are selected as merger candidates, i.e., treated as a single event for purposes of activation onset detection. Based on a user-selected or system-defined window-of-interest, submitted at step 320, valid annotations are chosen at step 322 from the merged candidates obtained in step 314.

Figure 32:
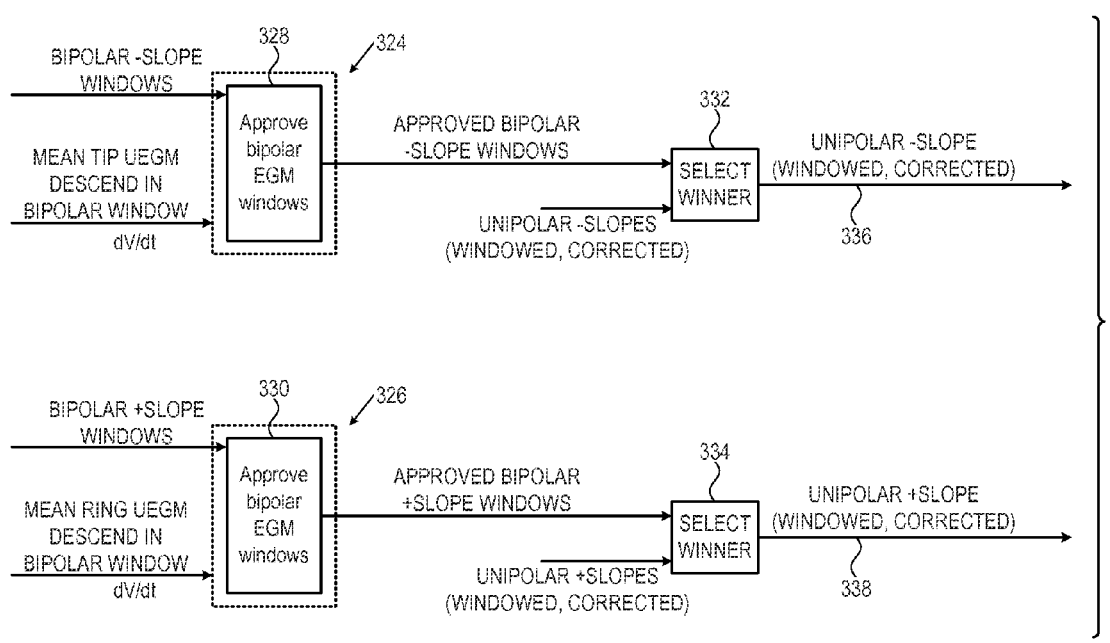
FIG. 32 shows data flow diagrams embodying a portion of the method of FIG. 27, in accordance with an embodiment of the invention.

Reference is now made to FIG. 32, which shows data flow diagrams 324, 326 illustrating detection of local activation times based on unipolar electrograms (UEGM) within accepted bipolar search windows, in accordance with an embodiment of the invention. Bipolar windows are approved when a slope within the window (dV/dt) is below a predefined negative threshold. Diagrams 324, 326 apply to unipolar tip and ring electrodes, respectively. Both procedures are similar.

In blocks 328, 330, negative and positive bipolar slope windows are approved for tip and ring unipolar electrodes within the windows, respectively. In blocks 332, 334 windows that were approved in blocks 328, 330, and the corrected unipolar electrogram slopes for positive and negative electrodes from output 218 (FIG. 24) are applied, respectively. Outputs 336, 338 are optimum negative and positive corrected windowed slopes, respectively. It will be recalled that the steepest slopes are selected. However other selection strategies can be used, e.g., based on other characteristics of the unipolar electrogram.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. An apparatus, comprising:
electrical circuitry for recording signal data from electrodes of a probe when the probe is at a location in a heart of a living subject, the signal data comprising a bipolar electrogram and a unipolar electrogram;
a memory for storing the signal data;
a display; and
a processor connected to the memory and operative for performing the steps of:
defining a time interval comprising a window-of-interest;
differentiating the bipolar electrogram and the unipolar electrogram with respect to time to define a differentiated bipolar electrogram and a differentiated unipolar electrogram, respectively;
identifying peaks within the window-of-interest in the differentiated bipolar electrogram;
establishing a bipolar activity window about respective peaks, the bipolar activity window having activity bounds and comprising a time interval of activity about the peaks in the bipolar electrogram; and identifying an extreme negative value (−dV/dt) in the differentiated unipolar electrogram within the activity bounds, and reporting a time corresponding to the value as a unipolar activation onset on the display;

wherein identifying an extreme negative value comprises:

defining a slope window in the unipolar electrogram that contains downward sloping intervals;

fitting respective regression lines to the downward sloping intervals;

determining a trend in the slope window, the trend having a slope;

identifying a longest monotonic downward sloping interval contained in each slope window;

making a determination that the longest monotonic downward sloping interval occupies less than 50% of its containing slope window; and responsive to the determination, subtracting the slope of the trend from a slope of the regression line of the longest monotonic downward sloping interval.

2. The apparatus according to claim 1, wherein the electrical circuitry further comprises a filter to remove baseline wander from the unipolar electrogram.

3. The apparatus according to claim 1, further comprising the step of adjusting slopes of the regression line by subtracting the slope of the trend therefrom.

4. A method, comprising the steps of:

providing an apparatus according to claim 1;

inserting a probe into a heart of a living subject, the probe having electrodes;

recording a bipolar electrogram and a unipolar electrogram from a location in the heart with the electrodes; defining a time interval comprising a window-of-interest;

differentiating the bipolar electrogram and the unipolar electrogram with respect to time to define a differentiated bipolar electrogram and a differentiated unipolar electrogram, respectively;

identifying peaks within the window-of-interest in the differentiated bipolar electrogram;

establishing a bipolar activity window about respective peaks, the bipolar activity window having activity bounds that include activity about the peaks in the bipolar electrogram; and identifying an extreme negative value (−dV/dt) in the differentiated unipolar electrogram within the activity bounds, and reporting a time corresponding to the value as a unipolar activation onset.

5. The method according to claim 4, further comprising the steps of: filtering the unipolar electrogram to remove baseline wander therefrom.

6. The method according to claim 4, wherein identifying an extreme negative value comprises:

defining a slope window in the unipolar electrogram that contains downward sloping intervals;

fitting respective regression lines to the downward sloping intervals; determining a trend in the slope window, the trend having a slope; identifying a longest monotonic downward sloping interval contained in each slope window;

making a determination that the longest monotonic downward sloping interval occupies less than 50% of its containing slope window; and responsive to the determination subtracting the slope of the trend from a slope of the regression line of the longest monotonic downward sloping interval.

7. The method according to claim 4, further comprising the steps of:

iterating the steps of identifying peaks, establishing a bipolar activity window and identifying an extreme negative value using time-reversed versions of the bipolar electrogram and the differentiated unipolar electrogram as the differentiated bipolar electrogram to yield a new extreme negative value; and reporting a time corresponding to the new extreme negative value as a unipolar activation termination.

8. The method according to claim 4, wherein establishing a bipolar activity window comprises:

defining baseline segments between complexes of the bipolar electrogram; identifying the complexes by executing a state machine; and assigning a transition between the baseline segments and the complexes as a boundary of the bipolar activity window.

9. The method according to claim 4, wherein establishing a bipolar activity window comprises:

classifying segments in the bipolar electrogram as being above or below a predefined value; and identifying a transition from one of the segments to another of the segments as a boundary of the bipolar activity window.

10. An apparatus, comprising:

electrical circuitry for recording signal data from electrodes of a probe when the probe is at a location in a heart of a living subject, the signal data comprising a bipolar electrogram and a unipolar electrogram;

a memory for storing the signal data;

a display; and a processor connected to the memory and operative for performing the steps of:

differentiating the bipolar electrogram and the unipolar electrogram with respect to time to define a differentiated bipolar electrogram and a differentiated unipolar electrogram;

respectively assigning times corresponding to minima in the differentiated unipolar electrogram as candidate annotation points, wherein the minima are less than a predefined negative threshold value;

defining respective time intervals about the minima in the differentiated unipolar electrogram;

determining that during at least one of the previously defined time intervals the bipolar electrogram or the differentiated bipolar electrogram fails to meet a criterion of correlated activity with the differentiated unipolar electrogram, the at least one time interval then being defined as an uncorrelated time interval;

defining qualified candidate annotation points by excluding candidate annotation points that lie within the at least one uncorrelated time interval;

establishing an annotation point as an activation onset time in the unipolar electrogram from among the qualified candidate annotation points; and reporting the annotation point, which corresponds to the activation onset time, on the display.

11. The apparatus according to claim 10, wherein the electrical circuitry comprises a median filter.

12. The apparatus according to claim 10, wherein the processor is operative for establishing an annotation point by a process further comprising the steps of:

determining that a plurality of the qualified candidate annotation points constitute a single activity according to a predetermined single activity criterion;

merging the plurality of the qualified candidate annotation points into a merged candidate annotation; and selecting one annotation point from one of the merged candidate annotation and others of the qualified candidate annotation points.

13. The apparatus according to claim 12, wherein the single activity criterion comprises a determination that a peak in the differentiated unipolar electrogram lies between two qualified candidate annotation points, and that a ratio between (1) a difference between the peak and one of the two qualified candidate annotation points and (2) another of the two qualified candidate annotation points exceeds a predefined ratio.

14. A method, comprising the steps of:
providing an apparatus according to claim 10;
inserting a probe into a heart of a living subject, the probe having electrodes;
recording a bipolar electrogram and a unipolar electrogram from a location in the heart with the electrodes;
differentiating the bipolar electrogram and the unipolar electrogram with respect to time to define a differentiated bipolar electrogram and a differentiated unipolar electrogram;
respectively assigning times corresponding to minima in the differentiated unipolar electrogram as candidate annotation points, wherein the minima are less than a predefined negative threshold value;
defining respective time intervals about the minima; determining that during at least one of the time intervals the bipolar electrogram or the differentiated bipolar electrogram fails to meet a criterion of correlated activity with the differentiated unipolar electrogram;
defining qualified candidate annotation points by excluding candidate annotation points that lie within the at least one time interval;
establishing an annotation as an activation onset time in the unipolar electrogram from among the qualified candidate annotation points; and
reporting the annotation.

15. The method according to claim 14, further comprising the steps of adjusting the bipolar electrogram and the unipolar electrogram to null baseline portions thereof.

16. The method according to claim 15, wherein adjusting comprises filtering the unipolar electrogram with a median filter.

17. The method according to claim 15, wherein adjusting comprises filtering the bipolar electrogram with a median filter.

18. The method according to claim 14, wherein the criterion of correlated activity comprises a variation of amplitude in the bipolar electrogram.

19. The method according to claim 18, wherein the variation of amplitude is at least 0.008 mV.

20. The method according to claim 14, wherein the criterion of correlated activity comprises a failure of a slope of the bipolar electrogram to exceed −0.008 mV/ms.

21. The method according to claim 14, wherein the criterion of correlated activity comprises a ratio between a slope of the bipolar electrogram and a slope of the unipolar electrogram that exceeds 0.2.

22. The method according to claim 14, wherein the criterion of correlated activity comprises a ratio between an amplitude of the bipolar electrogram and an amplitude of the unipolar electrogram that exceeds a predetermined value.

23. The method according to claim 14, wherein the time intervals have boundaries located ±2 ms from the candidate annotation points.

24. The method according to claim 14, wherein a slope of the unipolar electrogram at the candidate annotation points does not exceed −0.01 mV/ms.

25. The method according to claim 14, wherein establishing an annotation comprises the steps of:
determining that a plurality of the qualified candidate annotation points constitute a single activity according to a predetermined single activity criterion;
merging the plurality of the qualified candidate annotation points into a merged candidate annotation; and
selecting one annotation from the merged candidate annotation and others of the qualified candidate annotation points.

26. The method according to claim 25, wherein the single activity criterion comprises a determination that a peak in the differentiated unipolar electrogram lies between two qualified candidate annotation points and a ratio between (1) a difference between the peak and one of the two qualified candidate annotation points and (2) another of the two qualified candidate annotation points exceeds a predefined ratio.

* * * * *